(12) United States Patent
Nakanishi et al.

(10) Patent No.: US 9,090,755 B2
(45) Date of Patent: Jul. 28, 2015

(54) ORGANOPOLYSILOXANE POLYMER, PASTY COMPOSITION, AND COSMETIC PREPARATION CONTAINING THE COMPOSITION

(75) Inventors: Tetsuo Nakanishi, Gunma (JP); Koji Sakuta, Gunma (JP); Kiyomi Tachibana, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 2514 days.

(21) Appl. No.: 10/527,671

(22) PCT Filed: Sep. 11, 2003

(86) PCT No.: PCT/JP03/11613

§ 371 (c)(1),
(2), (4) Date: Mar. 11, 2005

(87) PCT Pub. No.: WO2004/024798

PCT Pub. Date: Mar. 25, 2004

(65) Prior Publication Data

US 2006/0034875 A1   Feb. 16, 2006

(30) Foreign Application Priority Data

Sep. 12, 2002 (JP) .................................. 2002-266357

(51) Int. Cl.
*A61Q 19/00* (2006.01)
*A61K 8/89* (2006.01)
*C08K 5/103* (2006.01)
*A61K 8/891* (2006.01)
*A61K 8/892* (2006.01)
*A61K 8/894* (2006.01)
*A61Q 1/02* (2006.01)
*A61Q 1/06* (2006.01)
*A61Q 1/10* (2006.01)
*A61Q 5/00* (2006.01)
*A61Q 5/06* (2006.01)
*A61Q 5/12* (2006.01)
*A61Q 15/00* (2006.01)
*A61Q 17/04* (2006.01)
*C08K 5/01* (2006.01)
*C08K 5/5419* (2006.01)

(52) U.S. Cl.
CPC .................. *C08K 5/103* (2013.01); *A61K 8/891* (2013.01); *A61K 8/892* (2013.01); *A61K 8/894* (2013.01); *A61Q 19/00* (2013.01); *A61Q 1/02* (2013.01); *A61Q 1/06* (2013.01); *A61Q 1/10* (2013.01); *A61Q 5/00* (2013.01); *A61Q 5/06* (2013.01); *A61Q 5/12* (2013.01); *A61Q 15/00* (2013.01); *A61Q 17/04* (2013.01); *C08K 5/01* (2013.01); *C08K 5/5419* (2013.01)

(58) Field of Classification Search
CPC ....................................................... A61K 8/894
See application file for complete search history.

(56) References Cited

U.S. PATENT DOCUMENTS

| | | | |
|---|---|---|---|
| 4,906,686 A | 3/1990 | Suzuki et al. | |
| 5,023,288 A | 6/1991 | Hirai et al. | |
| 5,144,054 A * | 9/1992 | Shioya et al. ................. | 556/445 |
| 6,150,311 A | 11/2000 | Decoster et al. | |
| 6,365,670 B1 | 4/2002 | Fry | |
| 6,388,005 B1 | 5/2002 | Morita et al. | |
| 6,461,597 B1 | 10/2002 | Morita et al. | |
| 6,531,542 B1 | 3/2003 | Morita et al. | |
| 6,747,115 B2 * | 6/2004 | Sakuta ........................... | 528/31 |
| 2003/0199660 A1 | 10/2003 | Sakuta | |
| 2004/0253197 A1 | 12/2004 | Sakuta | |

FOREIGN PATENT DOCUMENTS

| | | |
|---|---|---|
| EP | 0 326 712 A2 | 8/1989 |
| EP | 0350951 | 1/1990 |
| EP | 0350951 A | 1/1990 |
| EP | 0966945 A | 12/1999 |
| EP | 1074575 | 2/2001 |
| EP | 1074575 A | 2/2001 |
| EP | 1101487 | 5/2001 |
| EP | 1101487 A | 5/2001 |
| EP | 1103574 | 5/2001 |
| EP | 1103574 A | 5/2001 |
| EP | 1132430 | 9/2001 |
| EP | 1291376 | 3/2003 |
| EP | 1424365 | 6/2004 |
| JP | 2002114663 | 4/2002 |
| WO | WO 0192375 | 6/2001 |
| WO | WO 01/92375 | * 12/2001 |
| WO | WO 03020828 | 3/2003 |

OTHER PUBLICATIONS

Patent Abstracts of Japan vol. 2002, No. 08, Aug. 5, 2002.

* cited by examiner

*Primary Examiner* — David J Blanchard
*Assistant Examiner* — Tigabu Kassa
(74) *Attorney, Agent, or Firm* — Millen, White, Zelano & Branigan, P.C.

(57) ABSTRACT

An organopolysiloxane polymer having a glycerol derivative which can swell up by containing at least its own weight of a liquid oil, a pasty composition comprising a liquid oil blended with this polymer, and a cosmetic material containing these polymers or pasty compositions.

31 Claims, No Drawings

ORGANOPOLYSILOXANE POLYMER, PASTY COMPOSITION, AND COSMETIC PREPARATION CONTAINING THE COMPOSITION

FIELD OF THE INVENTION

The present invention relates to a hydrophilic organopolysiloxane polymer which has a glycerol derivative, to a pasty composition comprising this organopolysiloxane polymer and a liquid oil, and a cosmetic composition in which this pasty composition is blended.

BACKGROUND OF THE INVENTION

Silicone oil is used as a base oil of various compositions in many fields such as cosmetics due to its safety. In particular, in skin care and makeup, silicone oil having a low viscosity of 100 $m^2/s$ or less is receiving attention due to its outstanding extensibility, fresh feel and safety, and many companies are considering using it.

However, if low viscosity silicone oil is used as a base oil, for example to prepare a non-flowing pasty composition, the addition amount of thickener must be increased, so a smooth, uniform composition is hard to obtain. Also, since the low viscosity silicone oil easily separates from the composition, there is a problem of low stability.

In order to solve these problems, in the prior art, it was proposed to use organic substances such as dextrin fatty acid ester (Japanese Patent Application Laid-Open (JP-A) Nos. S62-121764, S62-143971, S62-143970, S63-159489), sucrose fatty acid ester (JP-A No. S63-235366), trimethylsilylated polyvinyl alcohol or trimethylsilylated polysaccharides (JP-A No. S62-240335), cellulose ether containing fatty acid ester groups (JP-A No. S63-260955), or inorganic substances such as organic-modified clay minerals (JP-A Nos. S62-45656, S62-54759, S63-72779), as thickeners for low viscosity silicone oil.

However, when these organic or inorganic substances are used as thickeners, there is a problem in that the properties which the low viscosity silicone oil originally had, such as fresh feel and extensibility, decline. A specific silicone polymer was therefore proposed as a thickener, wherein this was treated with a low viscosity silicone oil under a shear force in order to obtain a uniform pasty composition (JP-A No. H02-43263).

In the field of cosmetics, in addition to oils, water is often blended as a required ingredient. In such a case, although a surfactant is used, it is difficult to distribute the silicone oil and water in a homogenous and stable state by conventional methods. The silicone thickener disclosed in JP-A No. H02-43263 also had excellent thickening properties with respect to silicone oil, but it did not give a uniform dispersion when water was blended in. Moreover, some surfactants cause skin irritation, which is undesirable.

In order to resolve this problem, in Japanese Patent (JP-B) No. 2631772 and JP-A No. H05-140320, it is proposed to introduce a polyoxyalkylene group into the molecule of the silicone thickener. The composition disclosed here has the problem that although it has excellent emulsifying properties, the pH falls when the composition is stored for a long time, and the emulsion produced an unpleasant odor.

To resolve this issue, the polyether-modified silicone can be purified by treating it with an acidic aqueous solution (Japanese Patent Application Publication (JP-B) No. H07-91389), or unsaturated groups in the silicone can be hydrogenated (JP-A No. H07-330907). However, these purification techniques are applied to crosslinked polymers, and if they are treated with corrosive acidic aqueous solutions such as aqueous hydrochloric acid, if a glass-lined apparatus is not used, there is a risk that the apparatus will be corroded. Also, even if the unpleasant odor is reduced by this method, the fall of pH due to the characteristic autoxidation of the polyoxyethylene chain cannot be prevented, nor the fall in viscosity and rancid odor due to decomposition of the polyoxyethylene chain. The aforesaid problems can be controlled by addition of antioxidants, but their effect is not sufficient. Moreover, heavy metal catalysts such as palladium and nickel which are used to perform hydrogenation treatment cannot be removed by filtration purification, and since these heavy alloy catalysts remain in the composition, they render it unfit for use in cosmetics.

To resolve the aforesaid problems, the Inventors discovered that:

(1) polymers containing glycerol as a hydrophilic organic group have better solubility and emulsifying properties in various oils than organopolysiloxane polymers having a polyoxyalkylene chain, and (2) by adding an acidic substance to this glycerol-containing polymer or a pasty composition comprising this polymer and a liquid oil, performing heat treatment, neutralizing with a basic substance and removing the volatile ingredients, a composition with good storage stability free from any unpleasant odor is obtained, and this led to the present invention.

It is therefore a first object of the present invention to provide a hydrophilic polysiloxane polymer having emulsifying properties.

It is therefore a second object of the present invention to provide a pasty composition having emulsifying properties which has very high storage stability and is free from any unpleasant odor.

It is a third object of the present invention to provide a cosmetic material which is free from any unpleasant odor, which is very pleasant to use, and which has excellent long-term stability.

SUMMARY OF THE INVENTION

The aforesaid purposes of the invention are provided by an organopolysiloxane polymer having a glycerol derivative, by an organopolysiloxane polymer which can swell up by containing at least its own weight of a liquid oil, by a pasty composition using this polymer, and by a cosmetic material containing these preparations. According to the present invention, the amount of propionaldehyde generated when an equivalent amount of water is added to this composition and it is heated to 60° C. for 24 hours, can be reduced to 100 ppm or less. The cosmetic material containing this pasty composition has excellent long-term stability, has the clean feeling unique to silicone, and leaves the skin moist. The pasty composition of the present invention may be a simple mixture of an organopolysiloxane polymer and liquid oil, or the organopolysiloxane polymer and liquid oil may be kneaded together.

DETAILED DESCRIPTION OF THE INVENTION

The hydrophilic organopolysiloxane polymer of the present invention is obtained by addition polymerization of the organohydrogen polysiloxane expressed by the following general formula (a1) and/or following general formula (a2), with one or more compounds selected from a group comprising glycerol derivatives having an alkenyl group expressed by the following general formula (b1), organopolysiloxanes having an alkenyl group expressed by the following general formula (b2), and hydrocarbons having an alkenyl group expressed by the following general formula (b3), wherein the ingredients expressed by the aforesaid general formula (a1) or (b1) are essential ingredients.

$$R^1_a R^2_b H_c SiO_{(4-a-b-c)/2} \quad (a1)$$

$$R^1_d H_e SiO_{(4-d-e)/2} \quad (a2)$$

$$R^3_f G \quad (b1)$$

$$R^1_p R^3_q SiO_{(4-p-q)/2} \quad (b2)$$

$$R^3(CH_2)_r R^3 \quad (b3)$$

The ingredient (a1) is expressed by the average formula $R^1_a R^2_b H_c SiO_{(4-a-b-c)/2}$. In the formula, $R^1$ is a substituted or unsubstituted monovalent hydrocarbon group having 1-30 carbon atoms which does not have an alkenyl group. This group may be alkyl, aryl, aralkyl or a halogenated hydrocarbon. Specific examples are alkyl groups such as methyl, ethyl, propyl, butyl, pentyl, hexyl, heptyl, octyl, nonyl, decyl, stearyl and behenyl; saturated cycloaliphatic hydrocarbon groups such as cyclopentyl and cyclohexyl; aryl groups such as phenyl or tolyl; aralkyl groups such as phenethyl; or fluorine-substituted alkyl group such as trifluoropropyl, nonafluorohexyl and heptadecylfluorodecyl.

$R^2$ is a monovalent group having a glycerol derivative G, preferably the glycerol derivative expressed by the general formula —$C_xH_{2x}G$. Herein, $C_xH_{2x}$ is a bivalent hydrocarbon wherein X is 2-20. Specific examples of $C_xH_{2x}$ are —(CH$_2$)$_2$—, —(CH$_2$)$_3$—, —CH$_2$CH(CH$_3$)CH$_2$—, —(CH$_2$)$_4$—, —(CH$_2$)$_5$—, —(CH$_2$)$_6$—, —(CH$_2$)$_7$—, —(CH$_2$)$_8$—, —(CH$_2$)$_2$—CH(CH$_2$CH$_2$CH$_3$)— and —CH$_2$—CH(CH$_2$CH$_3$)—.

As an example of $R^2$, the following glycerol ether may be mentioned. The $C_xH_{2x}$ group is preferably present at the end of the organic group, but $C_xH_{2x}$ may be combined with a hydroxyl group inside the glycerol chain as in the glycerol derivative shown by the following formulae:

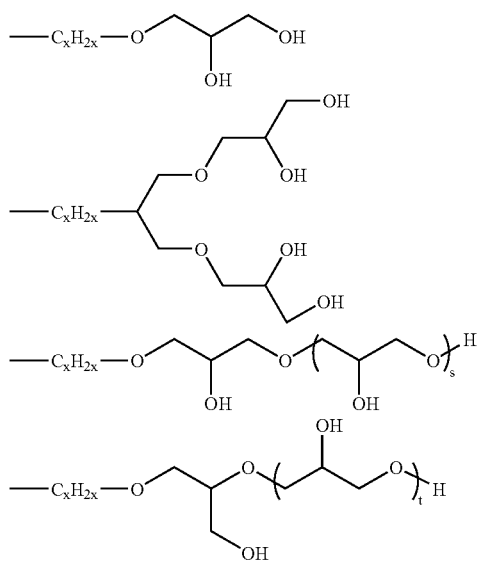

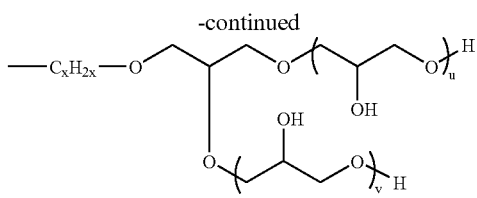

s, t, u, v in the above formulae representing the glycerol compound are integers in the range 1-20, but preferably 1-10. Part of the hydroxyl groups may be substituted by an alkoxy or ester group.

The aforesaid glycerol derivative may be a glycerol derivative having 1 mole of allyl groups which can be synthesized by, for example, reacting glycerol and glycidyl ether. A polyglycerol derivative can be obtained by reacting glycerol mono-allyl ether as starting material with several moles of glycidol. $R^2$ can be introduced by making this allylated polyglycerol undergo an addition reaction according to the usual method.

The ingredient (a1) is expressed by the general formula $R^1_a R^2_b H_c SiO_{(4-a-b-c)/2}$. Herein, a is 1.0-2.3, but preferably 1.2-2.1; b is 0.001-1.0, but preferably 0.005-0.5; and c is 0.001-1.0, but preferably 0.005-0.5. If a is smaller than 1.0, the degree of crosslinking is too high, so the compound cannot contain its own weight or more of liquid oil, and if a is larger than 2.3, the degree of crosslinking is too low, so it is difficult to form a three-dimensional crosslinked structure. If b is smaller than 0.001, the hydrophilicity is low, so it is difficult to form a water-in-oil type (W/O) emulsifying composition. If it is larger than 1.0, the hydrophilicity is too high, so it is again difficult to form a water-in-oil type emulsifying composition.

If c is smaller than 0.001, the degree of crosslinking is low, so it is difficult to form a three-dimensional crosslinked structure. If it is larger than 1.0, the degree of crosslinking is too high, so the compound can no longer contain its own weight or more of liquid oil. a+b+c is 1.5-2.6, but preferably 1.8-2.2. This organopolysiloxane is preferably straight-chain or mainly straight-chain to make the polymerization reaction go smoothly, but it may be straight-chain with some branched units, branched or cyclic having $R^1SiO_{3/2}$, $SiO_2$ or the like as structural units.

A specific example of the ingredient (a1) is expressed by the following formulae:

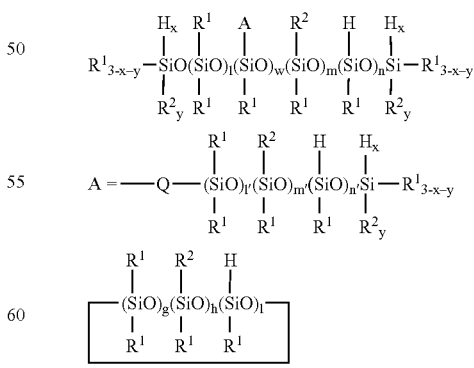

$R^1$ and $R^2$ express the aforesaid groups,
x, y are 0 or 1, and x+y=1.
$0 \le l \le 100$, $0 \le m \le 100$, $0 \le n \le 100$, $0 \le w \le 100$, $0 \le l' \le 100$, $0 \le m' \le 100$, $0 \leq n' \leq 100$, $0 \leq l+m+n \leq 200$,
$0 \leq l'+m'+n' \leq 200$, Q is an oxygen atom or a bivalent hydrocarbon group having 2-20 carbon atoms, $0 \leq g \leq 8$, $0 \leq h \leq 8$, $0 \leq i \leq 8$, $3 \leq g+h+i \leq 8$.

The ingredient (a2) is expressed by the general formula $R^1_d H_e SiO_{(4-d-e)/2}$.

Herein, d is 1.0-2.3, but preferably 1.2-2.1; and e is 0.001-1.0, but preferably 0.005-0.5.

If d is smaller than 1.0, the degree of crosslinking is too high, so the compound cannot contain its own weight or more of liquid oil, and if it is larger than 2.3, the degree of crosslinking is too low, so it is difficult to form a three-dimensional crosslinking structure. If e is smaller than 0.001, the degree of crosslinking is too low, so it is difficult to form a three-dimensional crosslinked structure. If it is larger than 1.0, the degree of crosslinking is too high, so the compound can no longer contain its own weight or more of liquid oil. This organopolysiloxane is preferably straight-chain or mainly straight-chain to make the polymerization reaction go smoothly, but it may be straight-chain with some branched units, branched, or cyclic having $R^1 SiO_{3/2}$, $SiO_2$ or the like as structural units.

Specific examples of the ingredient (a2) are expressed by the following formulae:

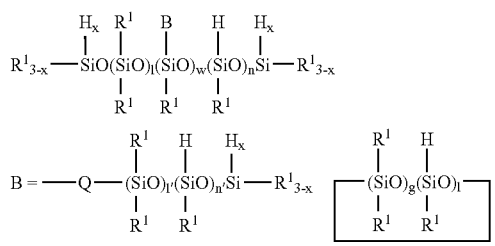

$R^1$ expresses the aforesaid group.

x, l, n, w, l', n', g, i are identical to the case of the aforesaid ingredient (a1), and $3 \leq g+i \leq 8$.

The ingredient (b1) is a glycerol derivative having an alkenyl group expressed by the general formula $R^3_f G$. $R^3$ is an aliphatic unsaturated hydrocarbon or alicyclic unsaturated hydrocarbon with an alkenyl group, having 2-20 carbon atoms. $R^3$ is a preferably a hydrocarbon group having an alkenyl group expressed by the general formula $C_y H_{2Y-1}$—. Y is an integer in the range 2-20. Examples of $C_y H_{2Y-1}$ are vinyl, 1-propenyl, allyl, isopropenyl, 1-butenyl, 2-butenyl, 3-butenyl, 2-methylallyl, 2-pentenyl, 4-pentenyl, 5-hexenyl and 10-undecenyl. Among these, vinyl and allyl where Y=2 or 3 are preferred. G is glycerol or polyglycerol, and the alkenyl group ($R^3$) in the glycerol derivative is preferably at the end of the derivative. f is an integer in the range 2-10, but preferably 2 or 3. This ingredient (b1) may be synthesized by an etherification reaction between the hydroxyl group of glycerol or polyglycerol, and an alkenyl alcohol or alkenyl glycidyl ether.

Examples of (b1) are the glycerol ethers expressed by the following formulae, but it may comprise mixtures thereof. The group $R^3$ is preferably present at the end of the glycerol derivative, but may be combined with a hydroxyl group inside the glycerol chain as in the glycerol derivative shown by the following formulae:

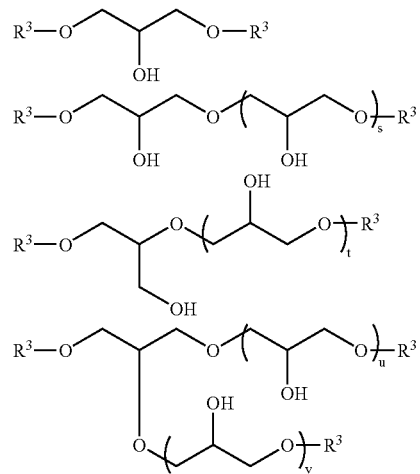

S, t, u, v are respectively integers in the range 1-20.

The ingredient (b2) may be expressed by the general formula $R^1_p R^3_q SiO_{(4-p-q)/2}$. $R^3$ is the alkenyl group of the ingredient (b1). Herein, p is 1.0-2.3, but preferably 1.2-2.1; and q is 0.001-1.0, but preferably 0.005-0.5. If p is smaller than 1.0, the degree of crosslinking is too high, so the compound cannot contain its own weight or more of liquid oil, and if it is larger than 2.3, the degree of crosslinking is too low, so it is difficult to form a three-dimensional crosslinked structure. If q is smaller than 0.001, the degree of crosslinking is too low, so it is difficult to form a three-dimensional crosslinked structure, and if it is larger than 1.0, the degree of crosslinking is too high, so the compound can no longer contain its own weight or more of liquid oil. This organopolysiloxane is preferably straight-chain or mainly straight-chain to make the polymerization reaction go smoothly, but it may be straight-chain with some branched units, branched, or cyclic having $R^1 SiO_3/2$, $SiO_2$ or the like as structural units.

The ingredient (b2) may be expressed by the following formulae:

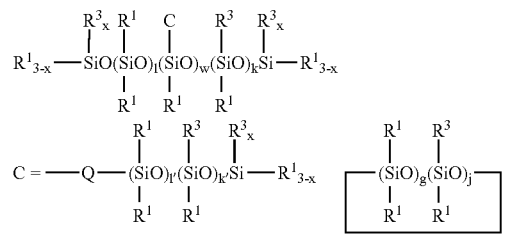

$R^1$ and $R^3$ express the aforesaid groups.

z is 0 or 1, $0 \leq k \leq 100$, $0 \leq k' \leq 100$, $0 \leq l+k \leq 200$, $0 \leq l'+k' \leq 200$, $1 \leq j \leq 8$, $3 \leq g+j \leq 8$.

The ingredient (b3) is expressed by the general formula $R^3(CH_2)_r R^3$, where $R^3$ is the alkenyl group of ingredient (b1) and r is an integer in the range 0-20. The ingredient (b3) may be a diene such as butadiene, pentadiene, hexadiene, heptadiene, octadiene and nonadiene, but hexadiene is particularly preferred.

The organopolysiloxane polymer of the present invention is a combination of (a1) with one or more of (b1)-(b3), a combination of (a1+a2) with one or more of (b1)-(b3), a combination of (a2) with (b1), a combination of (a2), (b1) and (b2), or a combination of (a2), (b1), (b2) and (b3), but preferred combinations are as follows. From the organopolysiloxane polymer of the present invention thus obtained, a pasty composition can be obtained by kneading with a liquid oil.
1. Combination of (a1) with (b2) or (b3)
2. Combination of (a2) with (b1)

To obtain the organopolysiloxane polymer of this invention, the ingredients may be reacted together in the presence of a platinum compound (e.g., chloroplatinic acid, alcohol-modified chloroplatinic acid or chloroplatinic acid-vinyl siloxane complex), or a rhodium compound, at room temperature or with heating (approx. 50-120° C.).

The reaction may be performed without a solvent, or an organic solvent may be used if required. Examples of this organic solvent are aliphatic alcohols such as methanol, ethanol, 2-propanol or butanol; aromatic hydrocarbons such as benzene, toluene or xylene; aliphatic or cycloaliphatic hydrocarbons such as n-pentane, n-hexane or cyclohexane; halogenated hydrocarbons such as dichloromethane, chloroform or carbon tetrachloride; and ketones such as acetone and methylethyl ketone. From the viewpoint of use in cosmetic materials, the reaction is best performed in the absence of a solvent, or using ethanol or 2-propanol as solvent.

To obtain the pasty composition of the present invention, the organopolysiloxane polymer is first synthesized, and then kneaded with a liquid oil. The polymer still containing the organic solvent used for the reaction may be purified by removing volatile ingredients such as the solvent and odorous substances, then the polymer kneaded with a liquid oil; or alternatively, the organopolysiloxane polymer may be kneaded with a liquid oil, and then purified.

The aforesaid purification is performed as required, e.g., it may be performed only with water without adding an acidic substance, but in order to control the reaction uniformly, it is preferably performed with the addition of an acidic substance selected from organic acids, inorganic acids and their salts. The addition amount of acidic substance added at this time is 0.01-10 weight parts, but preferably 0.02-5 weight parts, relative to 100 weight parts of organopolysiloxane polymer. If it is less than 0.01 weight parts, there is little deodorizing effect, and if it is more than 10 weight parts, neutral salts deposit in the composition after treatment which is undesirable. These organic acids may be added as they are, but are preferably added as a 1-50 weight parts aqueous solution. However, even if an organic acid aqueous solution is added to a polymer which does not contain a liquid oil, contact with the treatment solution is not very efficient, so it is difficult to increase the degree of purity and perform a neutralization reaction.

In the purification treatment, from the view point of contact efficiency, it is preferred to add 5-30 weight parts of the aqueous solution to 100 weight parts of crosslinked polymer. The pH of the aqueous solution of the acidic substance is 2-5, but if the pH is too low, undesirable reactions such as cleavage of the siloxane chain may occur. For this reason, a desirable pH range is 3-5.

Regarding the treatment conditions after addition of the acidic substance, although heating is unnecessary, it is preferred to heat to 20-150° C., but particularly 50-100° C.

Although the basic neutralizer may be added as it is, it is preferred to add it in the form of a 1-50 wt % aqueous solution. The addition amounts are preferably adjusted so that the functional group equivalents of the acidic substance and basic neutralizer are in the range 1/0.1-0.1/1 but preferably 1/0.3-0.3/1, and the pH after neutralization is 5-8.

The treatment conditions after basic neutralizer addition are 20-150° C., but preferably 20-80° C.

Specific examples of the acidic substance are citric acid, lactic acid, tartaric acid, malic acid, glutamic acid, acetic acid, glycine, potassium dihydrogenphosphate and succinic acid, but citric acid, lactic acid and glutamic acid are particuarly preferred.

Specific examples of the basic neutralizer are sodium carbonate, sodium hydrogen carbonate, sodium hydroxide, potassium hydroxide, disodium hydrogenphosphate and sodium acetate, but sodium carbonate, sodium hydrogen carbonate and sodium hydroxide are particularly preferred.

The acidic substance and basic neutralizer are preferably selected from among combinations such that the salt produced by neutralization has a pH buffer effect. Hence, not only is the unpleasant odor reduced, but the pH of the composition is also stabilized.

The organopolysiloxane polymer of the present invention has the ability to swell with at least its own weight of a liquid oil, and this can be confirmed as follows. The organopolysiloxane polymer is mixed with the same weight of liquid oil, and allowed to stand at room temperature. After standing, the sample is placed on a 100 mesh filter and it is confirmed that there is no separation of liquid oil even after leaving for 5 minutes.

To manufacture the pasty composition of the present invention, the organopolysiloxane polymer can be kneaded with the liquid oil by an ordinary stirrer, but kneading under a shearing force is preferred. This is because the organopolysiloxane polymer has a three-dimensional crosslinked structure which does not dissolve in solvents, and the organopolysiloxane polymer and liquid oil must be given sufficient dispersibility so that a smooth, pasty composition is obtained.

The kneading treatment can be performed for example by a 3-roll mill, 2-roll mill, side grinder, colloid mill, Gaulin homogenizer or disper, but a method using 3-rolls or a disper is preferred.

The liquid oil used in the present invention is suitable if it is fluid at 25° C. From the viewpoint of usefulness, a liquid oil having a kinematic viscosity of 1-10,000 $mm^2/s$ at 25° C. is preferred. Examples of the liquid oil are silicone oil, hydrocarbon oil, ester oil, natural animal and vegetable oils, and semi-synthetic oil.

Some typical silicone oils are expressed by the following general formula:

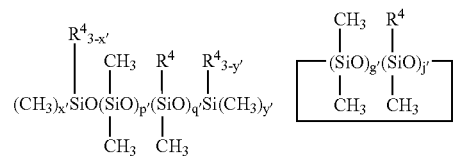

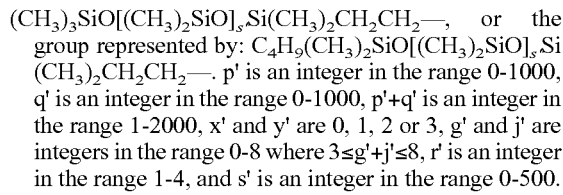

Herein, $R^4$ is a group selected from among a hydrogen atom, hydroxyl, monovalent unsubstituted or fluorinated alkyl group having 2-20 carbon atoms, aryl, amino-substituted alkyl, alkoxy, the group represented by the general formula:
$(CH_3)_3SiO[(CH_3)_2SiO]_sSi(CH_3)_2CH_2CH_2—$, or the group represented by: $C_4H_9(CH_3)_2SiO[(CH_3)_2SiO]_sSi(CH_3)_2CH_2CH_2—$. p' is an integer in the range 0-1000, q' is an integer in the range 0-1000, p'+q' is an integer in the range 1-2000, x' and y' are 0, 1, 2 or 3, g' and j' are integers in the range 0-8 where 3≤g'+j'≤8, r' is an integer in the range 1-4, and s' is an integer in the range 0-500.

Specific examples of $R^4$ are ethyl, propyl, butyl, hexyl, octyl, decyl, dodecyl, tetradecyl, hexadecyl, octadecyl, trifluoropropyl, nonafluorohexyl, heptadecylfluorodecyl, phenyl, aminopropyl, dimethylaminopropyl, aminoethylaminopropyl, stearoxy, butoxy, ethoxy, propoxy, cetyroxy, myristearoxy, styryl and α-methylstyryl, but hexyl, octyl, decyl, dodecyl, tetradecyl, hexadecyl, octadecyl, trifluoropropyl, phenyl, aminopropyl and amino ethylaminopropyl are preferred.

Examples of the silicone oil are organopolysiloxanes which are liquid at ordinary temperature ranging from low to high viscosity, such as dimethylpolysiloxane, methylphenylpolysiloxane, methylhydrogenpolysiloxane and dimethylsiloxane-methylphenyl siloxane copolymer, cyclosiloxanes such as octamethylcyclotetrasiloxane (D4), decamethylcyclopentasiloxane (D5), dodecamethylcyclohexasiloxane (D6), tetramethyltetrahydrogencyclotetrasiloxane (H4) and tetramethyltetraphenylcyclotetrasiloxane, branched siloxanes such as tristrimethylsiloxysilane (M3T), tetrakistrimethylsiloxysilane (M4Q) and tristrimethylsiloxyphenyl silane, higher alkoxy-modified silicones such as stearoxysilicone, alkyl-modified silicones, amino-modified silicones and fluorinated silicones.

Hydrocarbon oils may be straight-chain or cyclic. However, oils which are solid at ordinary temperature such as ceresine and vaseline are undesirable from the viewpoint of usage. Specific examples are α-olefin oligomers, light isoparaffin, light liquid isoparaffin, squalane, synthetic squalane, vegetable squalane, squalene, liquid paraffin and liquid isoparaffin.

Examples of an ester oil include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester and diisostearyl malic acid.

Among ester oils, examples of glyceride oils which can be mixed therein include acetoglyceride, triisooctanoic acid glyceride, triisostearic acid glyceride, triisopalmitic acid glyceride, tri-2-ethylhexanoic acid glyceride, monostearic acid glyceride, di-2-heptylundecanoic acid glyceride, trimyristic acid glyceride and myristic acid isostearic acid diglyceride.

Examples of a higher fatty acid which can be mixed therein include undecylenic acid, oleic acid, linoleic acid, linolenic acid, arachidonic acid, eicosapentaenoic acid (EPA), docosahexaenoic acid (DHA), isostearic acid and lactic acid. Examples of a higher alcohol which can be mixed therein include oleyl alcohol, isostearyl alcohol, hexyldodecanol, octyldodecanol, cetostearyl alcohol, 2-decyltetradecinol and monooleyl glyceryl ether (cerakyl alcohol).

Natural animal and vegetable oils but also semi-synthetic oils can be mixed in the present cosmetic material, with examples including avocado oil, almond oil, olive oil, liver oil, beef foot oil, apricot kernel oil, wheat germ oil, sesame oil, rice germ oil, rice bran oil, sasanqua oil, safflower oil, cinnamon oil, squalane, squalene, turtle oil, soybean oil, tea seed oil, tsubaki oil, evening primrose oil, corn oil, rape seed oil, Japanese tung oil, germ oil, persic oil, castor oil, castor oil fatty acid methyl ester, sunflower oil, grape seed oil, jojoba oil, macadamia nut oil, mink oil, meadowfoam oil, cottonseed oil, tricoconut oil fatty acid glyceride, peanut oil, liquid lanolin, lanolin alcohol acetate, lanolin fatty acid polyethylene glycol and egg yolk oil.

The mixing proportion of the organopolysiloxane polymer having a glycerol derivative as hydrophilic group with the liquid oil is preferably 1/20-20/1 (weight ratio, relative to liquid oil), but more preferably 1/10-1/1.

This invention is a cosmetic material formed by blending one of the aforesaid polymers or pasty compositions as ingredient (A). This cosmetic material may further contain at least one moiety selected from among a group comprising a different oil from the oil blended with the pasty composition as ingredient (B), water as ingredient (C), a compound having an alcoholic hydroxyl group in the molecule as ingredient (D), a water-soluble or water-swelling polymer as ingredient (E), a powder and/or a colouring agent as ingredient (F), a surfactant as ingredient (G), a composition comprising a non-hydrophilic crosslinking organosilicone polymer and a liquid oil as ingredient (H), and a silicone resin as ingredient (I).

The oil of ingredient (B) blended with the cosmetic material of the present invention may be a solid, semi-solid or liquid oil usually used in cosmetic materials. For example, in the case of a liquid oil, it may be the same liquid oil as that used in the pasty composition, a different liquid oil therefrom or a mixture thereof, specific examples being as follows.

This other oil may for example be a natural animal and vegetable oil/fat or semi-synthetic oil/fat such as linseed oil, insect wax, perilla oil, cacao butter, kapok wax, kaya oil, carnauba wax, candellila wax, beef tallow, beef bone fat, hydrogenated beef tallow, spermaceti, hydrogenated oil, sugar cane wax, shea butter, Chinese tung oil, jojoba wax, shellac wax, lard, rice-bran wax, horse fat, palm oil, palm kernel oil, hydrogenated castor oil, bayberry wax, beeswax, cotton wax, Japan wax, haze kernel oil, montan wax, coconut oil, hydrogenated coconut oil, mutton-tallow, lanolin, reduced lanolin, lanolin alcohol, hard lanolin, lanolin acetate, lanolin fatty acid isopropyl, POE lanolin alcohol ether, POE lanolin alcohol acetate and POE hydrogenated lanolin alcohol ether. POE means polyoxyethylene.

Examples of hydrocarbon oils are ozokerite, ceresine, paraffin, paraffin wax, polyethylene wax, polyethylene/polypropylene wax, pristane, polyisobutylene, microcrystalline wax and Vaseline; and those of a higher fatty acid include lauric acid, myristic acid, palmitic acid, stearic acid, behenic acid, isostearic acid and 12-hydroxystearic acid.

Examples of a higher alcohol which can be mixed therein include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol). Other examples are trimethylsiloxysilicic acid and cyclosiloxane solutions of trimethylsiloxysilicic acid.

Examples of fluorinated oils include perfluoropolyether, perfluorodecalin and perfluorooctane. The blending proportion of ingredient (B) is preferably within the range of 1-95 wt % of the whole cosmetic material.

Water may be blended with the cosmetic material of the present invention as ingredient (C) according to the purpose, and its blending amount is preferably within the range of 1-95 wt % of the whole cosmetic material.

The compound having an alcoholic hydroxyl group in the molecule which may be added to the cosmetic material of the present invention as ingredient (D) according to the purpose, may be a lower alcohol such as ethanol or isopropyl alcohol, a sugar alcohol such as sorbitol or maltose, a sterol such as cholesterol, sitosterol, phytosterol or lanosterol, or a polyhydric alcohol such as butylene glycol, propylene glycol, dibutylene glycol or pentyl glycol, but water-soluble monohydric alcohols or water-soluble polyhydric alcohols are mainly used. The blending amount is preferably within the range of 1-98 wt % of the whole cosmetic material.

Water-soluble or water-swelling polymers which may be added to the cosmetic material of the present invention as ingredient (E) according to the purpose, may be vegetable polymers, such as gum arabic, tragacanth, galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymer; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride. These water-soluble polymers also include film-forming agents such as polyvinyl alcohol or polyvinyl pyrrolidone. The blending amount of ingredient (E) is preferably within the range of 0.1-25 wt % of the whole cosmetic material.

The powder which may be added to the cosmetic material of the present invention as ingredient (F) according to the purpose, is not particularly limited as to shape (whether it is spherical, acicular or tabular), size (whether it is of the order of fume, fine grain or pigment), or structure (whether it is porous or nonporous), provided that it has so far been used in conventional cosmetic materials. For instance, inorganic powders, organic powders, surfactant metal salt powders, colored pigments, pearl pigments, metallic powder pigments and natural colors can be added to the present cosmetic material, if desired.

Examples of a usable inorganic powder include titanium oxide, zirconiumoxide, zincoxide, ceriumoxide, magnesiumoxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxie, boron nitride and silica.

Organic powders may be broadly divided into synthetic products and natural products. Synthetic products include styrene-acrylic acid copolymer, divinylbenzene-styrene copolymer, vinyl resin, urea resin, phenol resin, fluororesin, silicone resin, acrylic resin, melamine resin, epoxy resin and polycarbonate resin; natural products include microcrystalline fiber powder, cellulose, silk powder, starch powder and lauroyl lysine. Specific examples of synthetic products are polyamide powder, polyester powder, polyethylene powder, polypropylene powder, polystyrene powder, polyurethane powder, benzoguanamine powder, polymethylbenzoguanamine powder, tetrafluoroethylene powder, polymethylmethacrylate powder, nylon powder, 12-nylon, 6-nylon, the crosslinked spherical dimethylpolysiloxane fine powder having a crosslinked dimethylpolysiloxane structure disclosed in JP-A No. H03-93834, the crosslinked spherical polymethylsilsesquioxane fine powder disclosed in JP-A No. H03-47848, the fine powder obtained by covering a crosslinked spherical polysiloxane rubber surface with polymethylsilsesquioxane particles disclosed in JP-A No. H07-196815 and H09-20631, and hydrophobically-treated silica.

Examples of a usable surfactant metal salt powder (metal soap powder) include powders of zinc stearate, aluminum stearate, calcium stearate, magnesium stearate, zinc myristate, magnesium myristate, zinc cetylphosphate, calcium cetylphosphate and zinc sodium cetylphosphate.

The colorant added as ingredient (F) may be a pigment or a dye. Examples of a usable colored pigment include inorganic red pigments, such as iron oxide, iron hydroxide and iron titanate; inorganic brown pigments, such as y-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powder complexes of the inorganic pigments as recited above.

Examples of a usable pearl pigment include titanium oxide-coated mica, bismuth oxychloride, titanium oxide-coated bismuth oxychloride, titanium oxide-coated talc, fish scales, and titanium oxide-coated colored mica; and those of a usable metallic powder pigment include aluminum powder, copper powder and stainless powder.

Tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207; and natural pigments include powders of carminic acid, laccaic acid, carthamin, bradilin and crocin.

Among these powders and/or colorants, in the present invention, it is preferred that at least part is a crosslinked spherical dimethylpolysiloxane fine powder having a crosslinked dimethylpolysiloxane structure, a crosslinked spherical polymethylsilsesquioxane fine powder, or the fine powder obtained by covering a crosslinked spherical polysiloxane rubber surface with polymethylsilsesquioxane particles. Powders and/or colorants having a fluorine group are also widely used.

To the extent that it does not interfere with the effect of the invention, these powders may further comprise powder composites, powders treated with ordinary oils, silicone oils, fluorine compounds or surfactants, reactive organohydrogen polysiloxanes, organopolysiloxanes having a hydrolysable alkoxysiloxane group, and acrylic-silicone copolymers having a hydrolysable silyl group, one, two or more of these moieties being used as required. The blending amount of these powders is preferably within the range of is 0.1-99 wt % of the whole cosmetic material. In particular, the blending amount in the case of a powdered solid cosmetic material is preferably within the range of 80-99 wt % of the whole cosmetic material.

The surfactant added to the cosmetic material of the present invention as ingredient (G) according to the purpose, may be an anionic, cationic, non-ionic or amphoteric surfactant, and is not particularly limited in the present invention provided that it is generally used in cosmetic materials.

Specific examples of a usable anionic surfactant include fatty acid soap, such as sodium stearate or triethanolamine palmitate; alkyl ether carboxylic acids and salts thereof; salts of amino acid-fatty acid condensates; alkanesulfonates; alkenesulfonates; sulfonated fatty acid esters; sulfonated fatty acid amides; sulfonates of formaldehyde condensate type; alkylsulfates; higher secondary alcohol sulfates; alkyl and aryl ethersulfates; fatty acid ether sulfates, fatty acid alkylolamide sulfates; ether sulfates, such as Turkey red oil; alkyl phosphates; ether phosphates; alkyl aryl ether phosphates; amide phosphates; and active agents of N-acylamino acid type;

examples of a usable cationic surfactant include amine salts, such as alkylamie salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopoly-siloxanes (JP-B No. 2137062, JP-A No. H07-330907), organopolysiloxanes modified with both polyoxyalkylene and alkyl groups (JP-A No. S61-90732, JP-A No. H09-59386), the silicone-branched polyoxyalkylene-modified organopolysiloxane and the silicone-branched organopolysiloxane modified with both polyoxyalkylene and alkyl groups disclosed in JP-A No. 2001-055307, polyglycerol-modified organopolysiloxanes (JP-B No. S62-34039, JP-B No. 2613124, JP-B No. 2844453, JP-A No. 2002-179798), organopolysiloxanes modified with both polyglycerol and alkyl groups, the silicone-branched polyglycerol-modified organopolysiloxane and silicone-branched organopolysiloxane modified with both polyglycerol and alkyl groups disclosed in JP-A No. 2002-179798, alkanolamides, sugar ethers and sugar amides.

Examples of a usable amphoteric surfactant include betaine, aminocarboxylate, imdazoline derivatives and amidoamines.

Among these surfactants, straight-chain or branched organopolysiloxanes having a polyglycerol chain in the molecule or organopolysiloxanes which are modified with alkyl groups and surfactants for which HLB is 2-8, are preferred. The blending amount is preferably 0.1-20 wt %, but more preferably 0.2-10 wt %, of the whole cosmetic material.

The non-hydrophilic crosslinked organopolysiloxane polymer in the composition comprising a non-hydrophilic crosslinked organopolysiloxane polymer and a liquid oil which may be used as ingredient (H) in the cosmetic material of the present invention, may be a polymer which swells up by containing at least its own weight of a low viscosity silicone having a viscosity of 0.65 mm$^2$/sec (25° C.)-100.0 mm$^2$/sec (25° C.), or a polymer which swells up by containing at least its own weight of a liquid oil which may be a hydrocarbon oil such as liquid paraffin, squalane or isododecane, a glyceride oil such as trioctanone, or an ester oil.

This crosslinked organopolysiloxane is obtained by reacting an alkylhydrogen polysiloxane with a crosslinking agent having a reactive vinyl unsaturated group at the end of the molecular chain. Examples of the alkylhydrogen polysiloxane are methylhydrogen polysiloxane which may be straight-chain or partly containing branched units, methylhydrogen polysiloxane grafted with an alkyl chain having 6-20 carbon atoms, or methylhydrogen polysiloxane grafted with a polyoxyethylene chain. There must be an average of two or more hydrogen atoms bonded to silicon atoms in the molecule. Examples of the crosslinking agent are substances having two or more vinylic reactive sites in the molecule such as methylvinyl polysiloxane or $\alpha,\omega$-alkenyldiene, glycerine triaryl ether, polyoxyalkenylated glycerine triaryl ether, trimethyloylpropane triaryl ether and polyoxyalkenylated trimethyloylpropane triaryl ether. Further, this crosslinking organopolysiloxane preferably contains one or more moieties selected from a group comprising a polyoxyalkylene part, polyglycerol part, alkyl part, alkenyl part, aryl part or fluoroalkyl part in the molecule. The crosslinking agent is preferably one of those disclosed in JP-A No. H02-43263, JP-A No. H02-214775, JP-B No. 2631772, JP-A No. H09-136813 (KSG30), JP-A No. 2001-342255, International Publication No. WO03/20828 (KSG210) and International Publication No. WO03/24413 (KSG40).

The blending amount of this crosslinking organopolysiloxane used is preferably 0.1-50 wt %, but more preferably 1-30 wt %, of the total amount of cosmetic material. Specific examples are the silicone compositions disclosed in JP-B No. H06-55897 and JP-B No. 1925781, or the composition comprising a silicone polymer and an oil other than silicone oil disclosed in the same patent.

The silicone resin which may be added to the cosmetic material of the present invention as ingredient (I) according to the purpose is a gum or a solid at ordinary temperature which can dissolve in decamethylcyclopentasiloxane. The gum-like silicone resin is preferably a straight-chain silicone expressed by the general formula $(CH_3)_3SiO\{(CH_3)_2SiO\}_{t'}\{(CH_3)R^5SiO\}_{u'}Si(CH_3)_3$, wherein $R^5$ is selected from among a methyl group, an alkyl group having 6-20 carbon atoms, an alkyl group containing an amino group having 3-15 carbon atoms, a fluorinated alkyl group and an alkyl group containing a quartenary ammonium salt, t' is 1001-20,000, u' is 1-5,000, and t'+u' is 2,500-25,000.

The solid-type silicone resin is preferably a reticular silicone compound comprising any combination of trialkylsiloxy units (T units), dialkylsiloxy units (D units), monoalkylsiloxy units (M units) and quarternarysiloxy units (Q units), i.e., a MQ resin, MDQ resin, MTQ resin, MDTQ resin, TD resin, TQ resin or TDQ resin. A reticular silicone compound having one or more moieties selected from a group comprising a pyrrolidone part, a long-chain alkyl part, a polyoxyalkylene part and a fluoroalkyl part in the molecule is particularly preferred (JP-A No. 2000-234062, JP-B No. 3218872).

More specifically, the silicone resin which is added as ingredient (I) is preferably the acrylic/silicone graft or block copolymer acrylic silicone resin disclosed in JP-B No. 2704730, or the deodorized acrylic/silicone graft or block copolymer acrylic silicone resin disclosed in JP-A No. 2000-344829. An acrylic silicone resin containing one or more moieties selected from a group comprising a pyrrolidone part, a long-chain alkyl part, a polyoxyalkylene part, a fluoroalkyl part and an anionic part such as carbonic acid in the molecule, can also be used. This acrylic silicone resin is preferably a semi-solid or solid at ordinary temperature.

Silicone resins, such as gum-like silicon resins, acrylic silicone resins and reticular silicone compounds, may also be dissolved in low viscosity silicone oil, volatile silicone oil or other oils, but in all cases, the blending amount if this silicone resin is used is preferably 0.1-20 wt % and preferably 1-10 wt % of resin relative to the total amount of cosmetic material.

To the present cosmetic material, the ingredients used in general cosmetic materials, such as an oil-soluble gelling agent, clay minerals modified with organic compounds, resins, antiperspirants, ultraviolet absorbents, a moisture-holding agent, antiseptics, an antimicrobial agent, perfume, salts, antioxidants, pH regulators, a chelating agent, refrigerant, an anti-inflammatory agent, skin beautifying components (a skin whitener, a cell activator, a rough dry skin improver, a blood circulation promoter, a skin astringent and an anti-seborrheic agent), vitamins, amino acids, nucleic acids, hormonesk, clathrate compounds and hair firming agents, can be added so far as they have no adverse influence on the effects of the present invention.

Examples of an oil-soluble gelling agent which can be added include metal soaps, such as aluminum stearate, magnesium stearate and zinc myristate; amino acid derivatives, such as N-lauroyl-L-glutamic acid and α,γ-di-n-butylamine; dextrin fatty acid esters, such as dextrin palmitic acid ester, dextrin stearic acid ester and dextrin 2-ethylhexaminic acid-palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of an antiperspirant which can be added may be selected from among aluminum chlorohydrate, aluminum chloride, aluminum sesquichlorohydrate, zirconyl hydroxychloride, aluminum zirconium hydroxychloride and aluminum zirconium glycine complex.

Examples of an ultraviolet absorbent which can be added include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of an ultraviolet absorption and scattering agent which can be added are powders which absorb and scatter ultraviolet light such as fine particle titanium oxide, fine particle iron-containing titanium oxide, fine particle zinc oxide, fine particle cerium oxide and their complexes.

Examples of a moisture-holding agent which can be added include glycerin, sorbitol, propylene glycol, dipropylene glycol, 1,3-butylene glycol, glucose, xylitol, maltitol, polyethylene glycol, hyaluromic acid, chondroitin sulfuric acid, pyrrolidone carboxylic acid, polyoxyethylene glycoside, and polyoxypropylene methylglycoside.

Examples of an antiseptic agent which can be added include alkyl p-hydroxybenzoates, benzoic acid, sodium benzoate, sorbic acid, potassium sorbate and phenoxyethanol; and those of an antimicrobial agent which can be added include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide, photosensitive element and phenoxyethanol.

Examples of salts which can be added are organic salts, inorganic salts, amino salts and amino acid salts. Inorganic salts include the sodium salts, potassium salts, magnesium salts, calcium salts, aluminum salts, zirconium salts and zinc salts of inorganic acids such as hydrochloric acid, sulphuric acid, carbonic acid and nitric acid; organic salts include the salts of organic acids such as acetic acid, dehydroacetic acid, citric acid, malic acid, succinic acid, ascorbic acid and stearic acid; amino salts and aminoacid salts include the salts of amines such as triethanolamine, and salts of aminoacids such as glutamic acid. In addition, salts of hyaluronic acid and chondroitin sulfuric acid, aluminum zirconium glycine complex or acid-alkali neutralizing salts used in cosmetic preparations, can also be employed.

Examples of an antioxidant which can be added include tocopherol, butylhydroxyanisole, dibutylhydroxytoluene and phytic acid; those of a pH regulator which can be added include lactic acid, citric acid, glycolic acid, succinic acid, tartaric acid, dl-malic acid, potassium carbonate, sodium hydrogen carbonate and ammonium hydrogen carbonate; those of a chelating agent which can be added include alanine, sodium ethylenediaminetetraacetate, sodium polyphosphate, sodium metaphosphate and phosphoric acid; those of a refrigerant which can be added include L-menthol and camphor; and those of an anti-inflammatory agent which can added include allantoin, glycyrrhizin and salts thereof, glycyrrhetinic acid and stearyl glycyrrhetinate, tranexamic acid and azulene.

Examples of a skin-beautifying component which can be added include whitening agents, such as placenta extract, arbutin, glutathione and Yukinoshita extract; cell activators, such as royal jelly, photosensitive element, cholesterol derivatives and calf blood extract; rough dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol; skin astringents, such as zinc oxide and tannic acid; and anti-seborrheic agents, such as sulfur and thianthol.

Examples of vitamins which can be added include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as α-tocopherol, β-tocopherol, γ-tocopherol, dl-α-tocopheryl acetate, dl-α-tocopheryl nicotinate and dl-α-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of an aminoacid which can be added include glycine, valine, leucine, isoleucine, serine, threonine, phenylaranine, alginine, lysine, aspartic acid, aspartic acid, glutamic acid, cystine, cysteine, methionine, and tryptophan; those of a nucleic acid which can be added include deoxyribonucleic acid; and those of hormones which can be added include estradiol and ethenyl estradiol.

Examples of a hair firming polymer compound include amphoteric, anionic, cationic or nonionic polymer compounds, e.g. polyvinyl pyrrolidone-polymer compounds such as polyvinyl pyrrolidone and vinyl pyrrolidone/vinyl acetate copolymer, acidic vinyl ether polymer compounds such as methyl vinyl ether/maleic anhydride alkyl half ester copolymer, acidic polyvinyl acetate-polymers such as vinyl acetate/crotonic acid copolymer, acidic acrylic polymer compounds such as (meth)acrylic acid/alkyl(meth)acrylate copolymer and (meth)acrylic acid/alkyl(meth)acrylate/alkyl acrylamide copolymer, and amphoteric acrylic-polymer compounds such as N-methacryloylethyl-N,N-dimethyl ammonium-α-N-methyl carboxy betaine/alkyl(meth)acrylate copolymer, hydroxypropyl(meth)acrylate/butylaminoethylmethacrylate/acry lic acid octylamide copolymer. Also, naturally-occurring polymer compounds such as cellulose or its derivatives, keratin, and collagen or its derivatives, can also be used.

The term "cosmetic material" as used herein is intended to include skin care products, such as face lotion, milky lotion, cream, face cleansing cream, packs, oily liquid, massage material, rinsing agent, deodorants, hand cream and lip cream; makeup products such as foundation, powder, liquid foundation, oily foundation, rouge, eye shadow, mascara, eyeliner, eyebrow makeup and lipstick; and hairdressing products, such as shampoo, rinse, treatment and sets; antiperspirant, and ultraviolet defense cosmetic materials such as suncut milky lotion or suncut cream.

Additionally, the present cosmetic material may have any form, including liquid, emulsion, cream, solid, paste, gel, powder, compress, layers, mousse, spray or stick.

EXAMPLES

This invention will now be described referring to specific examples, but it will be understood that this invention is not to be construed as being limited in any way thereby. In the following general formulae, the $Me_3SiO_{1/2}$ group is referred to as M, the $Me_2SiO$ group is referred to as D, and the $MeSiO_{3/2}$ group is referred to as T. Units wherein a methyl group in M, D or T is modified by any substituent group are referred to as $M^R$, $D^R$, $T^R$. Further, unless otherwise specified, "%" in the following means "wt %".

A polyglycerol monoallylether (hereafter, G1) was prepared by condensing 1 mole of glycerol mono allylether with 2 moles of glycidol in the presence of a catalyst. The G1 obtained was a liquid having a viscosity of 3,000 mm$^2$/s, a hydroxyl value of 790 KOHmg/g and an unsaturation degree of 3.27 meq/g.

A polyglycerol diallylether (hereafter, G2) was prepared by condensing 1 mole of glycerine with 2 moles of alkylglycidyl ether in the presence of a catalyst. The G2 obtained was a liquid having a viscosity of 330 mm$^2$/s, a hydroxyl value of 509 KOHmg/g and an unsaturation degree of 6.20 meq/g.

Example 1

200.0 g of the organohydrogen polysiloxane expressed by the average formula $M_2D_{40}D^H_2$ as ingredient a2, 23.0 g of polyglycerol diallylether (G2) as ingredient b1, 148.7 g of dimethyl polysiloxane having a viscosity of 6 mm$^2$/s at 25° C., 74.3 g of isopropyl alcohol and 0.1 g of a 3 wt % ethanol solution of chlorplatinic acid, were introduced into a reaction vessel, and the mixture was stirred for 2 hours while the temperature was maintained at temperature at 70-80° C. to obtain an organopolysiloxane polymer.

Next, 43.5 g of a 1% citric acid aqueous solution was mixed in while maintaining the temperature at 70-80° C., and heating was continued for 3 hours. The reaction mixture was then cooled until the temperature fell to 50° C. or less, 7.0 g of 5% sodium hydrogen carbonate aqueous solution was added, and the reaction mixture was stirred for 1 hour while maintaining the temperature at 40-50° C. After stirring was complete, 0.11 g of d-6-tocopherol was added as antioxidant, the temperature was raised to 100° C. under reduced pressure, and volatile ingredients were removed to obtain an acid-treated organopolysiloxane polymer.

Next, this organopolysiloxane polymer was kneaded in a 3-roll mill, and diluted 2 times by adding dimethylpolysiloxane having a viscosity of 6 mm$^2$/s at 25° C. so as to obtain a pasty composition containing 30% of crosslinked material. This pasty material had a mixing consistency of 380 and a refractive index of 1.402.

Example 2

200.0 g of the organohydrogen polysiloxane containing a lauryl group expressed by the average empirical formula $M_2D_{40}D^{C12}_{10}D^H_3$ as ingredient a2, 18.3 g of polyglycerol diallylether (G2) as ingredient b1, 24.3 g of liquid paraffin, 48.5 g of isopropyl alcohol and 0.1 g of a 3 wt % ethanol solution of chlorplatinic acid, were introduced into a reaction vessel, and the mixture was stirred for 2 hours while the temperature was maintained at 70-80° C. to obtain an organopolysiloxane polymer.

Next, 43.7 g of a 1% citric acid aqueous solution and 121.2 g of liquid paraffin were mixed in while maintaining the temperature at 70-80° C., and the mixture was heated for 3 hours. The reaction mixture was then cooled until the temperature fell to 50° C. or less, 7.0 g of 5% sodium hydrogen carbonate aqueous solution was added, and the reaction mixture was stirred for 1 hour while maintaining the temperature at 40-50° C. After stirring was complete, 0.11 g of d-6-tocopherol was added as antioxidant, the temperature was raised to 100° C. under reduced pressure, and volatile ingredients were removed to obtain an acid-treated organopolysiloxane polymer.

Next, this organopolysiloxane polymer was kneaded in a 3-roll mill, and diluted 2 times by adding liquid paraffin so as to obtain a pasty composition containing 30% of crosslinked material. This pasty material had a mixing consistency of 390 and a refractive index of 1.450.

Example 3

200.0 g of the organohydrogen polysiloxane containing a lauryl group expressed by the average empirical formula $M_2D_{40}D^{C12}_{10}D^H_3$ as ingredient a2, 18.3 g of polyglycerol diallylether (G2) as ingredient b1, 327.5 g of glycerol triooctanoate, 109 g of isopropyl alcohol and 0.1 g of a 3 wt % ethanol solution of chlorplatinic acid, were introduced into a reaction vessel, and the mixture was stirred for 2 hours while the temperature was maintained at 70-80° C. to obtain an organopolysiloxane polymer.

Next, 43.7 g of a 1% citric acid aqueous solution was mixed in while maintaining the temperature at 70-80° C., and heating was continued for 3 hours. The reaction mixture was then cooled until the temperature fell to 50° C. or less, 7.0 g of 5% sodium hydrogen carbonate aqueous solution was added, and the reaction mixture was stirred for 1 hour while maintaining the temperature at 40-50° C. After stirring was complete, 0.11 g of d-δ-tocopherol was added as antioxidant, the temperature was raised to 100° C. under reduced pressure, and volatile ingredients were removed to obtain an acid-treated organopolysiloxane polymer.

Next, this organopolysiloxane polymer was kneaded in a 3-roll mill, and diluted 3 times by adding glyceryl trioctanoate so as to obtain a pasty composition containing 20% of crosslinked material. This pasty material had a mixing consistency of 400 and a refractive index of 1.442.

Example 4

200.0 g of the organohydrogen polysiloxane expressed by the average empirical formula $M_2D_{24}D^H_4$, 56.2 g of polyglycerol monoallylether (G1), 77 g of isopropyl alcohol and 0.05 g of a 3 wt % ethanol solution of chlorplatinic acid, were introduced into a reaction vessel, and the mixture was stirred for 2 hours while the temperature was maintained at 70-80° C. to obtain a polygylcerol-modified silicone $M_2D_{24}D^{Gly}_2D^H_2$ (Gly is a polyglycerol monoallylether residue).

Next, 200.0 g of the polglycerol-modified silicone $M_2D_{24}D^{Gly}_2D^H_2$ obtained as ingredient a1, 65.3 g of a silicone $M^{Vi}_2D_{10}$ having a vinyl group at both ends as ingredient b2, 177 g of dimethyl polysiloxane having a viscosity of 6 mm²/s at 25° C., 133 g of isopropyl alcohol and 0.1 g of a 3 wt % ethanol solution of chlorplatinic acid, were introduced into a reaction vessel, and the mixture was stirred for 2 hours while the temperature was maintained at 70-80° C. to obtain an organopolysiloxane polymer.

Next, 53.0 g of a 1% citric acid aqueous solution was mixed in while maintaining the temperature at 70-80° C., and heating was continued for 3 hours. The reaction mixture was then cooled until the temperature fell to 50 or less, 8.5 g of 5% sodium hydrogen carbonate aqueous solution was added, and the reaction mixture was stirred for 1 hour while maintaining the temperature at 40-50° C. After stirring was complete, 0.11 g of d-δ-tocopherol was added as antioxidant, the temperature was raised to 100° C. under reduced pressure, and volatile ingredients were removed to obtain an acid-treated organopolysiloxane polymer.

Next, this organopolysiloxane polymer was kneaded in a 3-roll mill, and diluted 2 times by adding dimethylpolysiloxane having a viscosity of 6 mm²/s at 25° C. so as to obtain a pasty composition containing 30% of crosslinked material. This pasty material had a mixing consistency of 395 and a refractive index of 1.403.

Example 5

200.0 g of the organohydrogen polysiloxane expressed by the average empirical formula $M_5T_3D_{53}D^H_3$, 19.5 g of polyglycerol monoallylether (G1), 66 g of isopropyl alcohol and 0.05 g of a 3 wt % ethanol solution of chlorplatinic acid, were introduced into a reaction vessel, and the mixture was stirred for 2 hours while the temperature was maintained at 70-80° C. to obtain the branched polyglycerol-modified silicone $M_5T_3D_{53}D^{Gly}D^H_2$ containing T units (Gly is a polyglycerol monoallylether residue).

Next, 200.0 g of the polyglycerol-modified silicone $M_5T_3D_{53}D^{Gly}D^H_2$ obtained as ingredient a1, 2.5 g of 1,5-hexadiene as ingredient b3, 135 g of dimethylpolysiloxane having a viscosity of 6 mm²/s at 25° C., 100 g of isopropyl alcohol and 0.1 g of a 3 wt % ethanol solution of chlorplatinic acid, were introduced into a reaction vessel, and the mixture was stirred for 2 hours while the temperature was maintained at 70-80° C. to obtain an organopolysiloxane polymer.

Next, 40.0 g of a 1% citric acid aqueous solution was mixed in while maintaining the temperature at 70-80° C., and heating was continued for 3 hours. The reaction mixture was then cooled until the temperature fell to 50° C. or less, 6.4 g of 5% sodium hydrogen carbonate aqueous solution was added, and the reaction mixture was stirred for 1 hour while maintaining the temperature at 40-50° C. After stirring was complete, 0.10 g of d-δ-tocopherol was added as antioxidant, the temperature was raised to 100° C. under reduced pressure, and volatile ingredients were removed to obtain an acid-treated organopolysiloxane polymer.

Next, this organopolysiloxane polymer was kneaded in a 3-roll mill, and diluted 2 times by adding dimethylpolysiloxane having a viscosity of 6 mm²/s at 25° C. so as to obtain a pasty composition containing 30% of crosslinked material. This pasty material had a mixing consistency of 410 and a refractive index of 1.403.

Example 6

W/O Type Milky Lotion

| (Ingredients) | Wt (%) |
|---|---|
| 1. Pasty composition of Example 1 | 10.0 |
| 2. Dimethylpolysiloxane (6 mm²/s (25° C.)) | 12.0 |
| 3. Decamethylcyclopenta siloxane | 10.0 |
| 4. Glyceryl trioctanoate | 5.0 |
| 5. 1,3-butylene glycol | 5.0 |
| 6. Antiseptic | suitable amount |
| 7. Perfume | suitable amount |
| 8. Purified water | 58.0 |

(Production Method)

A: Ingredients 1-5 were mixed homogeneously.

B: After mixing ingredients 6-8, they were added to A and the mixture emulsified.

The W/O type milky lotion obtained as described above was not tacky, spread lightly, adhered closely to the skin, compacted well and gave a lustrous finish.

Example 7

W/O Type Cream

| (Ingredients) | Wt (%) |
|---|---|
| 1. Pasty composition of Example 2 | 6.0 |
| 2. Liquid paraffin | 13.5 |
| 3. Macadamia nut oil | 4.0 |
| 4. Alkyl/polyether co-modified silicone (Note 1) | 1.5 |

-continued

| (Ingredients) | Wt (%) |
|---|---|
| 5. Sodium citrate | 0.2 |
| 6. Propylene glycol | 8.0 |
| 7. Glycerol | 3.0 |
| 8. Antiseptic | suitable amount |
| 9. Perfume | suitable amount |
| 10. Purified water | 60.8 |

(Note 1)
Shin-Etsu Chemical Co., Ltd: KF-6026 (product name)

(Production Method)

A: Ingredients 1-4 were mixed.

B: Ingredients 5-10 were mixed and dissolved, added to A and the mixture emulsified with stirring.

The W/O type cream obtained as described above was not tacky, spread lightly, had a clean feel, adhered closely to the skin, compacted well and gave a lustrous finish.

Example 8

W/O Type Cream

| (Ingredients) | Wt (%) |
|---|---|
| 1. Pasty composition of Example 3 | 7.0 |
| 2. Liquid paraffin | 13.5 |
| 3. Macadamia nut oil | 5.0 |
| 4. Alkyl/polyether co-modified silicone (Note 1) | 0.5 |
| 5. Hybrid silicone composition powder (Note 2) | 3.0 |
| 6. Sodium citrate | 0.2 |
| 7. Propylene glycol | 8.0 |
| 8. Glycerol | 3.0 |
| 9. Antiseptic | suitable amount |
| 10. Perfume | suitable amount |
| 11. Purified water | 59.8 |

(Note 1)
Shin-Etsu Chemical Co., Ltd.: KF-6026 (product name)
(Note 2)
Shin-Etsu Chemical Co., Ltd.: KSP-100 (product name)

(Production Method)

A: Ingredients 1-5 were mixed.

B: Ingredients 6-11 were mixed and dissolved, added to A and the mixture emulsified with stirring.

The W/O type cream obtained as described above was neither oily nor tacky, spread lightly and had a clean feel. It adhered closely to the skin, compacted well and gave a matte finish.

Example 9

W/O Type Cream

| (Ingredients) | Wt (%) |
|---|---|
| 1. Pasty composition of Example 1 | 7.0 |
| 2. Dimethylpolysiloxane (6 mm$^2$/s (25° C.)) | 10.0 |
| 3. Polyether-modified silicone (Note 1) | 0.5 |
| 4. Dipropylene glycol | 10.0 |
| 5. Sodium citrate | 0.2 |
| 6. Ethanol | 5.0 |
| 7. Antiseptic | suitable amount |
| 8. Perfume | suitable amount |
| 9. Purified water | 67.8 |

(Note 1)
Shin-Etsu Chemical Co., Ltd.: KF-6017 (product name)

(Production Method)

A: Ingredients 1-3 were mixed.

B: Ingredients 4-10 were mixed and dissolved, added to A and the mixture emulsified with stirring.

The W/O type cream obtained as described above was neither oily nor tacky, spread lightly and had a fresh, clean feel. It adhered closely to the skin, compacted well and gave a matte finish.

Example 10

W/O Type Cream

| (Ingredients) | Wt (%) |
|---|---|
| 1. Pasty composition of Example 2 | 3.0 |
| 2. Crosslinked alkyl dimethylpolysiloxane (Note 1) | 2.0 |
| 3. Alkyl/polyglycerol co-modified silicone (Note 2) | 0.5 |
| 4. Squalane | 14.5 |
| 5. Macadamia nut oil | 3.0 |
| 6. Hybrid silicone composition powder (Note 3) | 2.0 |
| 7. Sodium citrate | 0.2 |
| 8. Sodium chloride | 0.5 |
| 9. Dipropylene glycol | 8.0 |
| 10. Glycerol | 4.0 |
| 11. Antiseptic | suitable amount |
| 12. Perfume | suitable amount |
| 13. Purified water | 62.3 |

(Note 1)
Shin-Etsu Chemical Co., Ltd.: KSG-44 (product name)
(Note 2)
Shin-Etsu Chemical Co., Ltd.: KF-6105 (product name)
(Note 3)
Shin-Etsu Chemical Co., Ltd.: KSP-100 (product name)

(Production Method)

A: Ingredients 1-6 were mixed.

B: Ingredients 7-13 were mixed and dissolved.

C: B was added to A, and emulsified with stirring.

The W/O type cream obtained as described above was neither oily nor tacky, spread lightly and had a clean feel. It adhered closely to the skin, compacted well and gave a matte finish. The W/O type cream obtained as described above was neither oily nor tacky, spread lightly and had a clean feel. It adhered closely to the skin, compacted well and gave a matte finish.

Examples 11 and 12, and Comparative Examples 1 and 2

W/O Type Cream

W/O creams having the compositions shown in the following Table 1 were manufactured, and their use was evaluated.

TABLE 1

| | Ingredient | Example 11 | Example 12 | Comparative Example 1 | Comparative Example 2 |
|---|---|---|---|---|---|
| 1 | Pasty composition of Example 1 | 7 | 5 | — | — |
| 2 | Polyglycerol-modified silicone (Note 1) | — | 0.5 | — | — |
| 3 | Crosslinked polyether-modified silicone (Notes 2) | — | — | 7 | 5 |
| 4 | Polyether-modified silicone (Note 3) | — | — | — | 0.5 |
| 5 | Dimethylpolysiloxane (6 mm$^2$/s (25° C.)) | 18 | 11.5 | 18 | 11.5 |
| 6 | Dipropylene glycol | 10 | 10 | 10 | 10 |
| 7 | Sodium citrate | 0.2 | 0.2 | 0.2 | 0.2 |
| 8 | Sodium chloride | 0.5 | 0.5 | 0.5 | 0.5 |
| 9 | Ethanol | — | 5 | — | 5 |
| 10 | Antiseptic | Suitable amount | Suitable amount | Suitable amount | Suitable amount |
| 11 | Perfume | Suitable amount | Suitable amount | Suitable amount | Suitable amount |
| 12 | Purified water | 64.3 | 67.3 | 64.3 | 67.3 |

(Note 1)
Shin-Etsu Chemical Co., Ltd.: KF-6104
(Note 2)
Shin-Etsu Chemical Co., Ltd.: KSG-210
(Note 3)
Shin-Etsu Chemical Co., Ltd.: KF-6028

(Production Method)
A: Ingredients 1-5 were mixed.
B: Ingredients 6-12 were mixed.
C: B was added to A.
(Evaluation)
A test was conducted by a panel of 50 women. Spreadability, clean feel, absence of tackiness, moistness and long-term moistness were evaluated on the following basis, and assessed in terms of average points. Table 2 shows the results.
[Evaluation Basis]
    5 points: Very good
    4 points: Good
    3 points: Usual
    2 points: Rather poor
    1 point: Unsatisfactory
[Assessment]
    ⊚: 4.5 or more average points
    ○: 3.5 or more to less than 4.5 average points
    Δ: 2.5 or more to less than 3.5 average points
    X: Less than 2.5 average points

TABLE 2

| Evaluation criteria | Example 11 | Example 12 | Comparative Example 1 | Comparative Example 2 |
|---|---|---|---|---|
| Spreadability | ⊚ | ⊚ | ⊚ | ⊚ |
| Clean feel | ⊚ | ⊚ | ⊚ | ⊚ |
| Absence of tackiness after use | ⊚ | ⊚ | ⊚ | ⊚ |
| Moistness after use | ⊚ | ⊚ | Δ | Δ |
| Long-term moistness | ⊚ | ⊚ | Δ | Δ |

As can be seen from the results of Table 2, the W/O cream of Examples 11 and 12 containing the crosslinked polyglycerol-modified organopolysiloxane polymer of this invention excelled in moistness after use, and this moistness was maintained over time, as compared to the W/O cream of Comparative Examples 1 and 2. This is thought to be due to the fact that it has a water-holding capacity due to the glycerol group, and shows that the crosslinked polyglycerol-modified organopolysiloxane polymer of this invention or a mixture thereof with polyglycerol-modified silicone can provide a cosmetic material with high moisture retention which has excellent resistance to drying.

Example 13

W/O Type Milky Lotion

| (Ingredients) | Wt (%) |
|---|---|
| 1. Pasty composition of Example 1 | 0.5 |
| 2. Polyglycerol-modified silicone (Note 1) | 1.5 |
| 3. Dextrin fatty acid ester (Note 2) | 0.2 |
| 4. Fructoligosaccharide stearate (Note 3) | 1.8 |

| (Ingredients) | Wt (%) |
|---|---|
| 5. Dimethylpolysiloxane (6 mm²/s (25° C.)) | 6.0 |
| 6. Decamethylcyclopenta polysiloxane | 22.0 |
| 7. 1,3-butylene glycol | 7.0 |
| 8. Sodium citrate | 0.2 |
| 9. Ethanol | 5.0 |
| 10. Antiseptic | suitable amount |
| 11. Perfume | suitable amount |
| 12. Purified water | 55.8 |

(Note 1)
Shin-Etsu Chemical Co., Ltd.: KF-6104 (product name)
(Note 2)
Chiba Flour Milling Co., Ltd.: Reopar TT (product name)
(Note 3)
Chiba Flour Milling Co., Ltd.: Reopar ISK (product name)

(Production Method)
A: Ingredients 1-6 were mixed and heated.
B: Ingredients 7-12 were heated, mixed and dissolved, added to A, and the mixture was emulsified.

The W/O type milky lotion obtained as described above was neither oily nor tacky, spread lightly and had a fresh, clean feel. It adhered closely to the skin, compacted well, had a moist feeling and was very stable.

Example 14

O/W Type Cream

| (Ingredients) | Wt (%) |
|---|---|
| 1. Pasty composition of Example 3 | 8.0 |
| 2. Crosslinked methylphenyl polysiloxane (Note 1) | 2.0 |
| 3. Isotridecyl isononoate | 5.0 |
| 4. Dipropylene glycol | 7.0 |
| 5. Glycerol | 5.0 |
| 6. Methyl cellulose (2% aqueous solution) (Note 2) | 7.0 |
| 7. Polyacrylamide emulsifier (Note 3) | 2.0 |
| 8. Guanine | 1.0 |
| 9. Antiseptic | suitable amount |
| 10. Perfume | suitable amount |
| 11. Purified water | 63.0 |

(Note 1)
Shin-Etsu Chemical Co., Ltd.: KSG-18
(Note 2)
Shin-Etsu Chemical Co., Ltd.: Metrose SM-4000
(Note 3)
SEPPIC: Sepigel 305

(Production Method)
A: Ingredients 4-11 were mixed.
B: Ingredients 1-3 were mixed, A was added, and the mixture emulsified with stirring.

The W/O type milky lotion obtained as described above was fine, spread lightly, was neither tacky nor oily, and felt moist and fresh. It had a clean feel, lasted very well, showed no change with temperature or time, and was very stable.

Example 15

O/W Type Cream

| (Ingredients) | Wt (%) |
|---|---|
| 1. Pasty composition of Example 1 | 2.0 |
| 2. Crosslinked dimethylpolysiloxane (Note 1) | 28.0 |
| 3. Decamethylcyclopenta siloxane | 10.0 |
| 4. Dimethylpolysiloxane (6 mm²/s (25° C.)) | 5.0 |
| 5. Polyglycerol-modified silicone (Note 2) | 0.7 |
| 6. 1,3-butylene glycol | 3.0 |
| 7. Polyacrylamide mixture (Note 3) | 0.8 |
| 8. Polio oxyethylene hardening castor oil | 0.5 |
| 9. Water-soluble polymer (5% aqueous solution) (Note 4) | 10.0 |
| 10. Sodium chloride | 0.1 |
| 11. Antiseptic | suitable amount |
| 12. Perfume | suitable amount |
| 13. Purified water | 39.9 |

(Note 1)
Shin-Etsu Chemical Co., Ltd.: KSG-16 (product name)
(Note 2)
Shin-Etsu Chemical Co., Ltd.: KF-6100 (product name)
(Note 3)
SEPPIC: Sepigel 305 (product name)
(Note 4)
Client product: Aristoflex AVC (product name)

(Production Method)
A: Ingredients 1-4 were mixed.
B: Ingredients 5-13 were mixed and dissolved.
C: A was added to B, and the mixture emulsified with stirring.

The W/O type milky lotion obtained as described above was fine, spread lightly, was neither tacky nor oily, and felt moist and fresh. It had a clean feel, lasted very well, showed no change with temperature or time, and was very stable.

Example 16

O/W Type Cream

| (Ingredients) | Wt (%) |
|---|---|
| 1. Pasty composition of Example 1 | 2.0 |
| 2. Crosslinked dimethylpolysiloxane (Note 1) | 15.0 |
| 3. Decamethylcyclopentasiloxane | 10.0 |
| 4. Dimethylpolysiloxane (6 mm²/s (25° C.)) | 18.0 |
| 5. Polyether-modified silicone (Note 2) | 0.7 |
| 6. Propylene glycol | 3.0 |
| 7. Polyacrylamide mixture (Note 3) | 0.8 |
| 8. Xanthan gum (2% aqueous solution) | 8.0 |
| 9. Antiseptic | suitable amount |
| 10. Perfume | suitable amount |
| 11. Purified water | 42.5 |

(Note 1)
Shin-Etsu Chemical Co., Ltd.: KSG-16 (product name)
(Note 2)
Shin-Etsu Chemical Co., Ltd.: KF-6011 (product name)
(Note 3)
SEPPIC: Sepigel 305 (product name)

(Production Method)
A: Ingredients 1-4 were mixed.
B: Ingredients 5-11 were mixed and dissolved.
C: A was added to B, and the mixture emulsified with stirring.

The W/O type cream obtained as described above was fine, spread lightly, was neither tacky nor oily, and felt moist and fresh. It had a clean feel, lasted very well, showed no change with temperature or time, and was very stable.

Example 17

W/O Type Makeup Base

| (Ingredients) | Wt (%) |
|---|---|
| 1. Pasty composition of Example 4 | 5.0 |
| 2. Crosslinked dimethylpolysiloxane (Note 1) | 1.0 |
| 3. Polyether-modified silicone (Note 2) | 0.5 |
| 4. Dimethylpolysiloxane (6 mm$^2$/s (25° C.)) | 6.0 |
| 5. Dimethylpolysiloxane (20 mm$^2$/s (25° C.)) | 2.0 |
| 6. Decamethylcyclopentasiloxane | 3.0 |
| 7. Titanium oxide/cyclopentasiloxane dispersion (Note 3) | 10.0 |
| 8. Dipropylene glycol | 5.0 |
| 9. Sodium citrate | 0.2 |
| 10. Methyl cellulose (2% aqueous solution) (Note 4) | 2.5 |
| 11. Ethanol | 3.0 |
| 12. Antiseptic | suitable amount |
| 13. Perfume | suitable amount |
| 14. Purified water | 62.8 |

(Note 1)
Shin-Etsu Chemical Co., Ltd.: KSG-15 (product name)
(Note 2)
Shin-Etsu Chemical Co., Ltd.: KF-6017 (product name)
(Note 3)
Shin-Etsu Chemical Co., Ltd.: SPD-T 1S (product name)
(Note 4)
Shin-Etsu Chemical Co., Ltd.: Metrose65-SH4000 (product name)

(Production Method)
A: Ingredients 1-7 were mixed.
B: Ingredients 8-15 were mixed and dissolved, added to A, and the mixture emulsified with stirring.

The W/O type makeup base obtained as described above was neither oily nor tacky, spread lightly, and had a fresh, clean feel. It adhered closely to the skin, compacted well, gave a matte finish, had a UV protective effect and lasted well.

Example 18

Lipstick

| (Ingredients) | Wt (%) |
|---|---|
| 1. Polyethylene wax | 12.0 |
| 2. Microcrystalline wax | 4.0 |
| 3. Polybutene | 5.0 |
| 4. Acrylate/dimethyl silicone copolymer (Note 1) | 12.0 |
| 5. Pasty composition of Example 3 | 7.0 |
| 6. Cetyl octanoate | 20.0 |
| 7. Cane sugar fatty acid ester | 3.0 |
| 8. Glyceryl triisostearate | 37.0 |
| 9. Pigment | suitable amount |
| 10. Antiseptic | suitable amount |
| 11. Perfume | suitable amount |

(Note 1)
Shin-Etsu Chemical Co., Ltd.: KP-561

(Production Method)
A: Ingredients 1-7, part of 8 and 10 were heated and mixed, and dissolved.
B: Ingredients 9 and the remainder of 8 were mixed homogeneously.
C: Ingredient 11 and B were added to A, and homogenized.

The lipstick obtained as described above spread lightly, was not oily or powdery, have give a clean feel, had good water resistance and water repellence, lasted well, and was very stable.

Example 19

Lipstick

| (Ingredients) | Wt (%) |
|---|---|
| 1. Candellila wax | 4.0 |
| 2. Polyethylene wax | 2.0 |
| 2. Microcrystalline wax | 3.0 |
| 3. Ceresin | 7.0 |
| 4. Acrylate/dimethyl silicone copolymer (Note 1) | 15.0 |
| 5. Pasty composition of Example 3 | 0.5 |
| 6. Polyglycerol-modified silicone (Note 2) | 2.0 |
| 7. Polyisobutene with water | 15.0 |
| 8. Maleic acid diisostearate | 12.0 |
| 9. Macadamia nut oil | 30.0 |
| 10. Isotridecyl isononoate | 10.0 |
| 11. Glyceryl triisostearate | 4.0 |
| 12. Pigment | suitable amount |
| 13. Antiseptic | suitable amount |
| 14. Perfume | suitable amount |

(Note 1)
Shin-Etsu Chemical Co., Ltd.: KP-561P
(Note 2)
Shin-Etsu Chemical Co., Ltd.: KF-6105 (product name)

(Production Method)
A: Ingredients 1-10, and 13 were heated, mixed and dissolved.
B: Ingredients 11 and 12 were mixed homogeneously.
C: Ingredient 14 and B were added to A, dissolved homogeneously, and molded.

The lipstick obtained as described above spread lightly, was not oily or powdery, had a moist clean feel, had good water resistance and water repellence, lasted well and was very stable.

Example 20

Powder Foundation

| (Ingredients) | Wt (%) |
|---|---|
| 1. Vaseline | 2.5 |
| 2. Squalane | 3.0 |
| 3. Pasty composition of Example 2 | 0.5 |
| 4. Glyceryl trioctanoate | 2.0 |
| 5. Siliconized mica | 40.0 |
| 6. Siliconized talc | remainder |
| 7. Siliconized titanium oxide | 10.0 |
| 8. Siliconized particulate titanium oxide | 5.0 |
| 9. Siliconized barium sulfate | 10.0 |
| 10. Pigment | suitable amount |
| 11. Fluorine-modified hybrid silicone composition powder (Note 1) | 2.0 |
| 12. Silicone powder (Note 2) | 2.5 |
| 13. Antiseptic | suitable amount |
| 14. Perfume | suitable amount |

(Note 1)
Shin-Etsu Chemical Co., Ltd.: KSP-200 (product name)
(Note 2)
Shin-Etsu Chemical Co., Ltd.: KMP-590 (product name)

(Production Method)
A: Ingredients 4-13 were mixed, and homogenized.
B: Ingredients 1-3 were mixed homogeneously, added to A, and homogenized.
C: Ingredient 14 was added to B, and press-molded to make a powder foundation.

The powder foundation obtained as described above was not tacky, and spread lightly. It adhered closely to the skin, compacted well and gave a glossy finish.

Example 21

Cream Foundation

| (Ingredients) | Wt (%) |
|---|---|
| 1. Pasty composition of Example 3 | 5.5 |
| 2. Glyceryl trioctanoate | 4.0 |
| 3. Dimethylpolysiloxane (6 mm$^2$/s (25° C.)) | 5.0 |
| 4. Decamethylcyclopentasiloxane | 6.0 |
| 5. Fluorine-modified hybrid silicone composition powder (Note 1) | 2.5 |
| 6. Pigment | 8.0 |
| 7. Acrylic silicone resin (Note 2) | 5.0 |
| 8. Dipropylene glycol | 5.0 |
| 9. Sodium citrate | 0.2 |
| 10. Antiseptic | suitable amount |
| 11. Perfume | suitable amount |
| 12. Purified water | 59.3 |

(Note 1)
Shin-Etsu Chemical Co., Ltd.: KSP-200 (product name)
(Note 2)
Shin-Etsu Chemical Co., Ltd.: KP-545 (product name)

(Production Method)
A: Ingredients 1-5 were mixed.
B: Ingredients 8-12 were mixed and dissolved, added to A, and the mixture emulsified with stirring.
C: Ingredients 6-7 were mixed, added to B and homogenized.

The cream foundation obtained as described above was not tacky, and spread lightly. It adhered closely to the skin, compacted well and gave a mat finish.

Example 22

W/O Type Compact Foundation

| (Ingredients) | Wt (%) |
|---|---|
| 1. Ceresin | 5.5 |
| 2. Microcrystalline wax | 1.0 |
| 3. Liquid paraffin | 3.0 |
| 4. Pasty composition of Example 3 | 9.0 |
| 5. Dicapric acid polypropylene glycol | 3.0 |
| 6. Alkyl polyether co-modified silicone (Note 1) | 1.0 |
| 7. Dimethylpolysiloxane (6 mm$^2$/s (25° C.)) | 15.5 |
| 8. Oil-treated titanium oxide | 10.0 |
| 9. Pigment | suitable amount |
| 10. Lecithin | 0.3 |
| 11. Mono-oleic acid polyoxyethylene sorbitan | 0.5 |
| 12. Dipropylene glycol | 8.0 |
| 13. Sodium citrate | 0.2 |
| 14. Purified water | remainder |

(Note 1)
Shin-Etsu Chemical Co., Ltd.: KF-6026 (product name)

(Production Method)
A: Ingredients 1-7 were heated and mixed.
B: Ingredients 8-12 were homogenized.
C: Ingredients 13-14 were mixed, B was added and homogenized, and the mixture was warmed.
D: C was added to A, and the mixture emulsified.

The W/O compact foundation obtained as described above was not oily although it contained a large amount of oil, was not tacky, spread lightly, and had a clean feel. It adhered closely to the skin, compacted well and lasted very well.

Example 23

Liquid Foundation

| (Ingredients) | Wt (%) |
|---|---|
| 1. Pasty composition of Example 1 | 3.5 |
| 2. Crosslinked dimethylpolysiloxane (Note 1) | 5.0 |
| 3. Polyether-modified silicone (Note 2) | 1.0 |
| 4. Organic-modified clay mineral (Note 3) | 1.2 |
| 5. Glyceryl trioctanoate | 5.0 |
| 6. Dimethylpolysiloxane (6 mm$^2$/s (25° C.)) | 6.5 |
| 7. Decamethylcyclopentasiloxane | 21.6 |
| 8. Organopolysiloxane (Note 4)-treated pigment | 10.0 |
| 9. Acrylic silicone resin (Note 5) | 1.5 |
| 10. Dipropylene glycol | 5.0 |
| 11. Sodium citrate | 0.2 |
| 12. Antiseptic | suitable amount |
| 13. Perfume | suitable amount |
| 14. Purified water | 59.3 |

(Note 1)
Shin-Etsu Chemical Co., Ltd.: KSG-15 (product name)
(Note 2)
Shin-Etsu Chemical Co., Ltd.: KF-6028 (product name)
(Note 3)
NL Industries: Benton 38 (product name)
(Note 4)
Shin-Etsu Chemical Co., Ltd.: KF-9909 (product name)
(Note 5)
Shin-Etsu Chemical Co., Ltd.: KP-575 (product name)

(Production Method)
A: Ingredients 1-5, part of 6 and part of 7 were mixed.
B: The remainder of ingredient 6, the remainder of ingredient 7, and ingredients 8 and 9 were mixed homogeneously.
C: Ingredients 10-14 were mixed and dissolved.
D: C was added to A, and the mixture emulsified with stirring.
E: B was added to D and homogenized.

The liquid foundation obtained as described above was not tacky, and spread lightly. It adhered closely to the skin, compacted well, gave a mat finish, and was very stable.

Example 24

Eye Shadow

| (Ingredients) | Wt (%) |
|---|---|
| 1. Sericite | 40.0 |
| 2. Mica | 10.0 |
| 3. Talc | remainder |
| 4. Titanium oxide | 10.0 |
| 5. Particulate titanium oxide | 5.0 |
| 6. Magnesium stearate | 3.0 |
| 7. Pigment | suitable amount |
| 8. Octyl dodecanol | 3.0 |
| 9. Dimethylpolysiloxane (6 mm$^2$/s (25° C.)) | 4.0 |
| 10. Pasty composition of Example 1 | 6.0 |
| 11. Antiseptic | suitable amount |
| 12. Perfume | suitable amount |

(Production Method)

A: Ingredients 8-11 were heated and mixed.

B: After mixing ingredients 1-7, A was added and mixed homogeneously.

The eye shadow obtained as described above was not tacky, and spread lightly. It adhered closely to the skin, compacted well, gave a glossy finish and lasted well.

Example 25

Cream Eye Shadow

| (Ingredients) | Wt (%) |
|---|---|
| 1. Acrylate/dimethylsilicone copolymer (Note 1) | 10.0 |
| 2. Acrylate/dimethyl silicone copolymer (Note 2) | 2.0 |
| 3. Pasty composition of Example 1 | 0.3 |
| 4. Polyglycerol-modified silicone (Note 3) | 1.5 |
| 5. Decamethylcyclopentasiloxane | 20.0 |
| 6. Organic-modified clay mineral (Note 4) | 1.2 |
| 7. Cetyl isooctanoate | 3.0 |
| 8. Nylon | 3.0 |
| 9. Talc | 4.0 |
| 10. Acrylic silicone resin (Note 5)-treated pigment | 20.0 |
| 11. Ethanol | 5.0 |
| 12. Purified water | 30.0 |

(Note 1)
Shin-Etsu Chemical Co., Ltd.: KP-545 (product name)
(Note 2)
Shin-Etsu Chemical Co., Ltd.: KP-561P (product name)
(Note 3)
Shin-Etsu Chemical Co., Ltd.: KF-6105 (product name)
(Note 4)
NL Industries: Benton 38 (product name)
(Note 5)
Shin-Etsu Chemical Co., Ltd.: KP-574 (product name)

(Production Method)

A: Ingredients 1-10 were mixed.

B: After mixing ingredients 10-11, they were added to A, and mixed homogeneously.

The eye shadow obtained as described above was not tacky, and spread lightly. It adhered closely to the skin, compacted well, gave a glossy finish, was moist and lasted well.

Example 26

Powder Eyebrow

| (Ingredients) | Wt (%) |
|---|---|
| 1. Vaseline | 2.5 |
| 2. Dimethylpolysiloxane (6 mm$^2$/s (25° C.)) | 1.5 |
| 3. Pasty composition of Example 5 | 0.5 |
| 4. Glyceryl trioctanoate | 4.0 |
| 5. Siliconized mica | 40.0 |
| 6. Siliconized talc | remainder |
| 7. Siliconized titanium oxide | 10.0 |
| 8. Siliconized barium sulfate | 15.0 |
| 9. Siliconized pigment | suitable amount |
| 10. Hybrid silicone composition powder (Note 1) | 1.5 |
| 11. Spherical polymethyl silsesquioxane powder (Note 2) | 2.5 |
| 12. Antiseptic | suitable amount |
| 13. Perfume | suitable amount |

(Note 1)
Shin-Etsu Chemical Co., Ltd.: KSP-100 (product name)
(Note 2)
Shin-Etsu Chemical Co., Ltd.: KMP-590 (product name)

(Production Method)

A: Ingredients 5-12 were mixed, and homogenized.

B: Ingredients 1-4 were mixed homogeneously, added to A and homogenized.

C: Ingredient 13 was added to B, and press-molded to obtain a powder eyebrow.

The eyebrow obtained as described above was not tacky, and spread lightly. It adhered closely to the skin, compacted well, gave a glossy finish and lasted well.

Example 27

Hair Cream

| (Ingredients) | Wt(%) |
|---|---|
| 1. Pasty composition of Example 1 | 2.0 |
| 2. Dimethylpolysiloxane (6 mm$^2$/s (25° C.)) | 5.0 |
| 3. Decamethylcyclopentasiloxane | 8.0 |
| 4. Stearyl trimethylammonium chloride | 1.5 |
| 5. Glycerol | 3.0 |
| 6. Propylene glycol | 5.0 |
| 7. Hydroxyethyl cellulose | 0.2 |
| 8. Antiseptic | suitable amount |
| 9. Perfume | suitable amount |
| 10. Purified water | 75.3 |

(Production Method)

A: Ingredients 1-3 were mixed.

B: Ingredients 4-8 and 10 were mixed homogeneously, and dissolved.

C: B was added to A, the mixture emulsified, cooled and ingredient 9 was added.

The hair cream obtained as described above had many advantages, i.e., it spread well when applied, left the hair supple, smooth, good-looking, moist and glossy. It was thus a superb all-round hair cream.

Example 28

Conditioning Mousse

| (Ingredients) | Wt(%) |
|---|---|
| 1. Pasty composition of Example 1 | 0.5 |
| 2. Dimethylpolysiloxane (6 mm$^2$/s (25° C.)) | 2.0 |
| 3. Crosslinked dimethylpolysiloxane (Note 1) | 0.5 |
| 4. Glyceryl trioctanoate | 1.5 |
| 5. Glycerol | 3.0 |
| 6. Stearyl methylbenzyl ammonium chloride | 0.5 |
| 7. Polyoxyethylene hardening castor oil | 0.5 |
| 8. Ethanol | 7.0 |
| 9. Antiseptic | suitable amount |
| 10. Perfume | suitable amount |
| 11. Purified water | remainder |
| 12. Liquefied petroleum gas | 5.0 |

(Note 1) Shin-Etsu Chemical Co., Ltd.: KSG-16 (product name)

(Production Method)

A: Ingredients 1-4 were mixed.

B: Ingredients 5-9 and 11 were mixed homogeneously.

C: B was added to A, the mixture emulsified, cooled and ingredient 10 was added.

D: An aerosol can was then filled with C to obtain a conditioning mousse.

The conditioning mousse obtained as described above was very moist, flexible and smooth, and had a good feeling with no oiliness. It adhered closely to the skin, compacted well and gave a mat finish.

Example 29

Vanishing Cream

| (Ingredients) | Wt(%) |
|---|---|
| 1. Pasty composition of Example 1 | 5.0 |
| 2. Crosslinked dimethylpolysiloxane (Note 1) | 55.0 |
| 3. Crosslinked dimethylpolysiloxane (Note 2) | 15.0 |
| 4. Decamethylcyclopentasiloxane | 15.0 |
| 5. Hybrid silicone composition powder (Note 3) | 8.0 |
| 6. Spherical polymethyl silsesquioxane fine particles (Note 4) | 2.0 |

(Note 1) Shin-Etsu Chemical Co., Ltd.: KSG-15 (product name)
(Note 2) Shin-Etsu Chemical Co., Ltd.: KSG-16 (product name)
(Note 3) Shin-Etsu Chemical Co., Ltd.: KSP-100 (product name)
(Note 4) Shin-Etsu Chemical Co., Ltd.: KMP-590 (product name)

(Production Method)
A: Ingredients 1-6 were mixed homogeneously.

The vanishing cream obtained as described above was neither tacky nor oily, left the skin feeling very moist, was non-greasy with a matte feeling, and was very stable.

Example 30

Roll-On Type Antiperspirant

| (Ingredients) | Wt(%) |
|---|---|
| 1. Pasty composition of Example 1 | 25.0 |
| 2. Dimethylpolysiloxane (6 mm$^2$/s (25° C.)) | 10.0 |
| 3. Crosslinked dimethylpolysiloxane (Note 1) | 15.0 |
| 4. Deca methylcyclopentasiloxane | 30.0 |
| 5. Aluminium zirconium tetrachlorohydrate | 20.0 |
| 6. Perfume | suitable amount |

(Note 1) Shin-Etsu Chemical Co., Ltd.: KSG-15 (product name)

(Production method)
A: Ingredients 1-4 were mixed
B: Ingredients 5 and 6 were added to A, and dispersed homogeneously.

The roll-on antiperspirant obtained as described above spread lightly, felt cool and clean, was neither tacky nor oily, showed no change with temperature or time, and was very easy to use and very stable.

Example 31

W/O Type Antiperspirant

| (Ingredients) | Wt(%) |
|---|---|
| 1. Pasty composition of Example 4 | 9.0 |
| 2. Decamethylcyclopentasiloxane | 7.0 |
| 3. Glyceryl trioctanoate | 8.0 |
| 4. 1,3-butylene glycol | 5.0 |
| 5. Sodium citrate | 0.2 |
| 6. Aluminium chlorohydrate | 20.0 |
| 7. Perfume | suitable amount |
| 8. Purified water | 50.8 |

(Production Method)
A: Ingredients 1-3 were mixed.
B: Ingredients 4-5 and 8 were mixed, ingredients 6 and 7 were added, and dissolved.
C: B was added to A, and the mixture emulsified with stirring.

The W/O type antiperspirant obtained as described above spread lightly, felt cool and clean, was neither tacky nor oily, showed no change with temperature or time, and was very easy to use and very stable.

Example 32

W/O Type UV Cut Cream

| (Ingredients) | Wt(%) |
|---|---|
| 1. Siliconized zinc oxide | 20.0 |
| 2. Acrylate/dimethylsilicone copolymer (Note 1) | 12.0 |
| 3. Decamethylcyclopentasiloxane | 20.0 |
| 4. Glyceryl trioctanoate | 3.0 |
| 5. Pasty composition of Example 2 | 7.0 |
| 6. Polyether-modified silicone (Note 2) | 1.0 |
| 7. Alkyl/polyether co-modified silicone (Note 3) | 1.0 |
| 8. Octyl methoxycinnamate | 6.0 |
| 9. Sodium citrate | 0.2 |
| 10. Dipropylene glycol | 3.0 |
| 11. Antiseptic | suitable amount |
| 12. Perfume | suitable amount |
| 13. Purified water | 26.8 |

(Note 1) Shin-Etsu Chemical Co., Ltd.: KP-545 (product name)
(Note 2) Shin-Etsu Chemical Co., Ltd.: KF-6017 (product name)
(Note 3) Shin-Etsu Chemical Co., Ltd.: KF-6026 (product name)

(Production Method)
A: Part of ingredient 3, and 4-8 were mixed.
B: Ingredients 9-11 and 13 were mixed, added to A, and the mixture emulsified with stirring.
C: Ingredients 1, 2 and the remainder of 3 were mixed and dispersed, ingredient 12 was added to B, and homogenized.

The W/O type UV cut cream obtained as described above spread lightly and cleanly, was neither tacky nor oily, appeared transparent, lasted well, showed no change with temperature or time, and was very easy to use and very stable.

Example 33

W/O Type UV Cut Milky Lotion

| (Ingredients) | Wt(%) |
|---|---|
| 1. Dimethylpolysiloxane (6 mm$^2$/s (25° C.)) | 5.0 |
| 2. Glyceryl trioctanoate | 2.0 |
| 3. Pasty composition of Example 1 | 6.0 |
| 4. Polyether-modified silicone (Note 1) | 1.0 |
| 5. Titanium oxide/decamethylcyclopentasiloxane dispersion (Note 2) | 30.0 |
| 6. Zinc oxide/decamethylcyclopentasiloxane dispersion (Note 3) | 30.0 |
| 7. Dipropylene glycol | 3.0 |

| (Ingredients) | Wt(%) |
|---|---|
| 8. Sodium citrate | 0.2 |
| 9. Antiseptic | suitable amount |
| 10. Perfume | suitable amount |
| 11. Purified water | 22.8 |

(Note 1) Shin-Etsu Chemical Co., Ltd.: KF-6017 (product name)
(Note 2) Shin-Etsu Chemical Co., Ltd.: SPD-T 1S (product name)
(Note 3) Shin-Etsu Chemical Co., Ltd.: SPD-Z1 (product name)

(Production Method)
A: Ingredients 1-4 were mixed.
B: Ingredients 7-9 and 11 were mixed and dissolved, added to A, and the mixture emulsified with stirring.
C: Ingredients 5, 6 and 10 were added to B, and homogenized.

The W/O type UV cut milky lotion obtained as described above spread lightly and cleanly, was neither tacky nor oily, appeared transparent, lasted well, showed no change with temperature or time, and was very easy to use and very stable.

Example 34

W/O Type UV Cut Milky Lotion

| (Ingredients) | Wt(%) |
|---|---|
| 1. Pasty composition of Example 1 | 3.0 |
| 2. Crosslinked organopolysiloxane (Note 1) | 2.0 |
| 3. Polyether-modified silicone (Note 2) | 1.0 |
| 4. Dimethylpolysiloxane (6 mm$^2$/s (25° C.)) | 5.0 |
| 5. Decamethylcyclopentasiloxane | 5.0 |
| 6. Isotridecyl isononoate | 4.0 |
| 7. Titanium oxide/decamethylcyclopentasiloxane dispersion (Note 3) | 25.0 |
| 8. Zinc oxide/decamethylcyclopenta siloxane dispersion (Note 4) | 35.0 |
| 9. Dipropylene glycol | 3.0 |
| 10. Sodium citrate | 0.2 |
| 11. Sodium chloride | 0.5 |
| 12. Antiseptic | suitable amount |
| 13. Perfume | suitable amount |
| 14. Purified water | 22.8 |

(Note 1) Shin-Etsu Chemical Co., Ltd.: KSG-15 (product name)
(Note 2) Shin-Etsu Chemical Co., Ltd.: KF-6028 (product name)
(Note 3) Shin-Etsu Chemical Co., Ltd.: SPD-T 1V (product name)
(Note 4) Shin-Etsu Chemical Co., Ltd.: SPD-Z 1S (product name)

(Production Method)
A: Ingredients 1-6 were mixed.
B: Ingredients 9-12 and 13 were mixed and dissolved.
C: B was added to A, and the mixture emulsified with stirring.
D: Ingredients 7, 8 and 13 were added to C, and homogenized.

The W/O type UV cut milky lotion obtained as described above spread lightly and cleanly, and was neither tacky nor oily. It was moist, appeared transparent, lasted well, showed no change with temperature or time, and was very easy to use and very stable.

Example 35

O/W Type UV Cut Cream

| (Ingredients) | Wt(%) |
|---|---|
| 1. Crosslinked organopolysiloxane (Note 1) | 5.0 |
| 2. Cetyl isooctanoate | 5.0 |
| 3. Pasty composition of Example 4 | 1.0 |
| 4. Titanium oxide/decamethylcyclopentasiloxane dispersion (Note 2) | 15.0 |
| 5. Polyether-modified silicone (Note 3) | 1.0 |
| 6. Polyether-modified silicone (Note 4) | 1.0 |
| 7. Acrylic acid amide type mixture (Note 5) | 2.0 |
| 8. Propylene glycol | 5.0 |
| 9. Methyl cellulose (2% aqueous solution) (Note 6) | 5.0 |
| 10. Antiseptic | suitable amount |
| 11. Perfume | suitable amount |
| 12. Purified water | 60.0 |

(Note 1) Shin-Etsu Chemical Co., Ltd.: KSG-18 (product name)
(Note 2) Shin-Etsu Chemical Co., Ltd.: SPD-T 1S (product name)
(Note 3) Shin-Etsu Chemical Co., Ltd.: KF-6027 (product name)
(Note 4) Shin-Etsu Chemical Co., Ltd.: KF-6011 (product name)
(Note 5) Seppic: Sepigel 305 (product name)
(Note 6) Shin-Etsu Chemical Co., Ltd.: Metrolose SM-4000 (product name)

(Production Method)
A: Ingredients 5-8, 10 and 12 were mixed.
B: Ingredients 1-3 were heated and mixed, added to A, and the mixture emulsified with stirring.
C: Ingredient 4 was added to B, ingredients 9 and 10 were added, and the mixture was homogenized.

The O/W type UV cut cream obtained as described above spread lightly and cleanly, was neither tacky nor oily, appeared transparent, lasted well, showed no change with temperature or time, and was very easy to use and very stable.

Example 36

Non-Aqueous Emulsion

| (Ingredients) | Wt(%) |
|---|---|
| 1. Crosslinked dimethylpolysiloxane (Note 1) | 30.0 |
| 2. Decamethylcyclopentasiloxane | 15.0 |
| 3. Dimethylpolysiloxane (6 mm$^2$/s (25° C.)) | 7.0 |
| 4. Pasty composition of Example 1 | 3.0 |
| 5. Dimethyldistearylammonium hectorite | 2.0 |
| 6. Sodium chloride | 0.1 |
| 7. 1,3-butylene glycol | 40.9 |

(Note 1) Shin-Etsu Chemical Co., Ltd.: KSG-15 (product name)

(Production method)
A: Ingredients 1-5 were mixed homogeneously.
B: Ingredients 6 and 7 were mixed.
C: B was added to A, and the mixture emulsified homogeneously.

It was found that the nonaqueous emulsion obtained as described above spread lightly, was neither tacky nor oily, left the skin feeling moist, and was very stable.

Example 37

W/O/W Type Cream

| (Ingredients) | Wt(%) |
|---|---|
| 1. Cetyl isooctanoate | 5.0 |
| 2. Pasty composition of Example 1 | 6.0 |
| 3. Decamethylcyclopentasiloxane | 5.0 |
| 4. Dioleic acid methyl glucose | 1.5 |
| 5. Isohexadecane | 3.5 |

| (Ingredients) | Wt(%) |
|---|---|
| 6. Magnesium sulfate | 0.5 |
| 7. Propylene glycol | 5.0 |
| 8. Purified water | 39.5 |
| 9. Cetyl alcohol | 1.0 |
| 10. PEG-10 soya sterol | 2.0 |
| 11. Antiseptic | suitable amount |
| 12. Perfume | suitable amount |
| 13. Purified water | 31.0 |

(Production Method)
A: Ingredients 6-8 were mixed.
B: Ingredients 1-5 were mixed, added to A, and the mixture emulsified with stirring.
C: Ingredients 9-11 and 13 were mixed, B was added with stirring, and the mixture emulsified.
D: Ingredient 12 was added to C and homogenized.

The W/O/W type cream obtained as described above spread lightly and cleanly, was neither tacky nor oily, appeared transparent, lasted well, showed no change with temperature or time, and was very easy to use and very stable.

Example 38

O/W/O Type Milky Lotion

| (Ingredients) | Wt(%) |
|---|---|
| 1. Glyceryl triisooctanoate | 15.0 |
| 2. Pasty composition of Example 3 | 8.0 |
| 3. Cane sugar monostearate | 3.0 |
| 4. Glycerol | 5.0 |
| 5. 1,3-butylene glycol | 5.0 |
| 6. Antiseptic | suitable amount |
| 7. Purified water | 60.0 |
| 8. Macadamia nut oil | 2.0 |
| 9. Cetylalcohol | 2.0 |
| 10. Perfume | suitable amount |

(Note 1)
Shin-Etsu Chemical Co., Ltd.: KSG-21 (product name)

(Production Method)
A: Ingredients 1-2 were mixed homogeneously.
B: Ingredients 3-7 were heated, mixed and homogenized.
C: Ingredients 8-10 were heated and mixed.
D: While stirring B, C was added, the mixture emulsified and cooled.
D: While stirring A, D was added and the mixture emulsified.

The O/W/O type milky lotion obtained as described above spread lightly and cleanly, was neither tacky nor oily, appeared transparent, lasted well, showed no change with temperature or time, and was very easy to use and very stable.

Example 39

O/W/O Type Liquid Foundation

| (Ingredients) | Wt(%) |
|---|---|
| 1. Pasty composition of Example 2 | 7.0 |
| 2. Decanoic acid propylene glycol | 5.0 |
| 3. Isopropyl myristate | 5.0 |
| 4. Pigment | 10.0 |
| 5. Hydrogenated phospholipid from egg yolk | 1.0 |
| 6. Glycerol | 2.0 |
| 7. 1,3-butylene glycol | 10.0 |
| 8. Antiseptic | suitable amount |
| 9. Purified water | 52.0 |
| 10. Squalane | 3.0 |
| 11. Cetylalcohol | 5.0 |
| 12. Perfume | suitable amount |

(Production Method)
A: Ingredients 1-3 were mixed homogeneously.
B: Ingredients 4-9 were heated, mixed and homogenized.
C: Ingredients 10-12 were heated and mixed.
D: While stirring B, C was added, the mixture emulsified and cooled.

The O/W/O liquid foundation obtained above spreads lightly and is neither tacky nor oily. It is clear, lasts well and does not change with temperature, and is moreover very easy to use and highly stable.

As a result of the aforesaid examples, the organopolysiloxane polymer containing a glycerol derivative of the present invention and the pasty composition comprising this polymer together with a liquid oil have good solubility and emulsion properties with regard to various oils. Moreover, they can stably contain water.

The pH of the purified organopolysiloxane polymer having a glycerol derivative of the present invention and the pasty composition comprising this polymer and a liquid oil does not tend to fall even when stored for long periods or left at high temperature. It was also found that the unpleasant odor which develops due to changes with time is largely suppressed even when the polymer or composition blended in an emulsion.

Cosmetic materials with which the pasty composition comprising the organopolysiloxane polymer of the present invention is blended are not tacky or heavy when applied, feel clean and spread lightly, and leave the skin feeling clean, smooth and moist. These results show that by using a glycerol derivative as a hydrophilic functional group according to this invention, the products obtained spread lightly and cleanly, and since there is no loss of moisture when they are applied, they confer suppleness, smoothness and emollient properties. These cosmetic materials are moreover very easy to use, give a natural glossy or matte finish, and have good stability over time.

INDUSTRIAL APPLICATION

Compared to crosslinked organopolysiloxane polymers containing a polyoxyalkylene chain, the organopolysiloxane polymer having a glycerol derivative according to the present invention and the pasty composition comprising this polymer together with a liquid oil have improved solubility in oils, emulsion properties and water-holding stability. Compared to crosslinked organopolysiloxane polymers containing a polyoxyalkylene chain, the pH of the purified hydrophilic organopolysiloxane polymer having a glycerol derivative according to the present invention does not tend to fall during long periods of storage or when left at high temperature. Also, the unpleasant odour due to time-dependent changes is largely suppressed even when blended with an emulsion. When this pasty composition is blended with cosmetic materials, these cosmetic materials acquire excellent stability. They have the unique clean feel of silicone products and leave the skin feeling moist, and since a glycerol derivative is used as a hydrophilic functional group, their moisture-holding properties are improved.

What is claimed is:

1. An organopolysiloxane polymer having a glycerol derivative which can swell up by containing at least its own weight of a liquid oil selected from the group consisting of hydrocarbon oil, ester oil, natural animal and vegetable oils, semi-synthetic oil, and silicone oil selected from the group consisting of dimethylpolysiloxane, methylphenylpolysiloxane, methylhydrogenpolysiloxane and dimethylsiloxane-methylphenyl siloxane copolymer, cyclosiloxanes, branched siloxanes, higher alkoxy-modified silicones, alkyl-modified silicones and amino-modified silicones, wherein fluorinated silicones are excluded, obtained by the addition polymerization of an organohydrogenpolysiloxane expressed by the following general formula $R^1_d H_e SiO_{(4-d-e)/2}$, with a glycerol derivative having alkenyl groups expressed by at least one of the following general formulae,

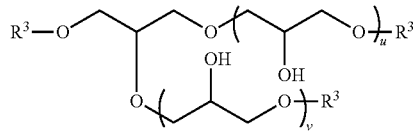

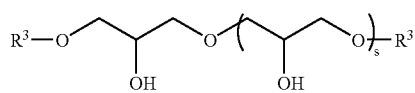

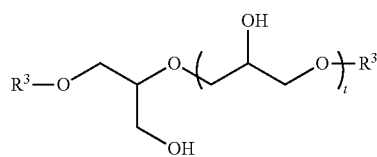

wherein, $R^1$ may be identical or different and is a substituted or unsubstituted monovalent hydrocarbon group having 1-30 carbon atoms which does not contain an alkenyl group, $R^3$ is an alkenyl group having 2-20 carbon atoms, d and e are respectively defined by:

$1.0 \leq d \leq 2.3$, $0.001 \leq e \leq 1.0$, $1.5 \leq d+e \leq 2.6$, and s, t, u and v are respectively integers in the range 1-20;

and wherein, the organopolysiloxane polymer has a three-dimensional cross-linked structure.

2. A pasty composition formed by containing a liquid oil in an organopolysiloxane having a glycerol derivative according to claim 1, whereby it swells up.

3. The pasty composition according to claim 2, wherein said liquid oil is one or more liquid oils selected from the group consisting of silicone oils, hydrocarbon oils, ester oils, natural animal and vegetable oils and semi-synthetic oils.

4. A composition formed by adding one or more acidic substances selected from the group consisting of organic acids, inorganic acids and inorganic acid salts to one or more polymers selected from the group consisting of the organopolysiloxane polymer having a glycerol derivative according to claim 1, or a pasty composition formed by containing a liquid oil in said organopolysiloxane having a glycerol derivative, whereby it swells up, adding a basic neutralizing agent so that the pH is 5-8, and then removing volatile ingredients by heating and/or reducing pressure.

5. The composition according to claim 4, wherein the salt produced from said acidic substance and said basic neutralizing agent has a buffer action.

6. The composition according to claim 4, wherein said acidic substance is one or more compounds selected from the group consisting of citric acid, lactic acid, malic acid, glutamic acid, oxalic acid, acetic acid, glycine, succinic acid and calcium dihydrogen phosphate, and said basic neutralising agent is one or more agents selected from the group consisting sodium carbonate, sodium hydrogen carbonate, sodium hydroxide, potassium hydroxide, di-sodium hydrogen phosphate and sodium acetate.

7. The composition according to claim 4, wherein the proportion of said acidic substance and said basic neutralising agent relative to 100 weight parts of said organopolysiloxane polymer is 0.01-10 weight parts, and to obtain said composition, the volatile ingredient is removed by heating to 20-150° C. after adding said acidic substance, and further heating to 20-150° C. and/or reducing pressure after adding said basic neutralising agent.

8. A cosmetic material formed by blending one or more polymers selected from the group consisting of the
polymers according to claim 1, or
pasty composition formed by containing a liquid oil in said organopolysiloxane having a glycerol derivative, whereby it swells up, or
composition formed by adding one or more acidic substances selected from the group consisting of organic acids, inorganic acids and inorganic acid salts to one or more polymers selected from the group consisting of said organopolysiloxane polymer having a glycerol derivative, or a pasty composition formed by containing a liquid oil in said organopolysiloxane having a glycerol derivative, whereby it swells up, adding a basic neutralizing agent so that the pH is 5-8, and then removing volatile ingredients by heating and/or reducing pressure,
as ingredient A).

9. The cosmetic material according to claim 8, further comprising an oil as ingredient B).

10. The cosmetic material according to claim 8, further comprising water as ingredient C).

11. The cosmetic material according to claim 8, further comprising a compound having an alcoholic hydroxyl group in the molecular structure as ingredient D).

12. The cosmetic material according to claim 8, further comprising a water-soluble or water-swelling polymer as ingredient E).

13. The cosmetic material according to claim 8, further comprising a powder and/or colorant as ingredient F).

14. The cosmetic material according to claim 13, wherein at least part of the powder and/or colorant which is ingredient F) is a powder selected from the group consisting of a crosslinked spherical dimethyl polysiloxane fine powder having a crosslinked dimethyl polysiloxane structure, a crosslinked spherical polymethyl silsesquioxane fine powder, and a fine powder formed by coating the surface of crosslinked spherical polysiloxane rubber particles with polymethylsilsesquioxane particles.

15. The cosmetic material according to claim 8, further comprising a surfactant as ingredient G).

16. The cosmetic material according to claim 15, wherein the surfactant of said ingredient G) is a straight-chain or branched organopolysiloxane having a polyglycerol chain in the molecule, or an alkyl co-modified organopolysiloxane.

17. The cosmetic material according to claim 15, wherein the HLB of said ingredient G) is 2-8.

18. The cosmetic material according to claim 8, further containing a composition comprising a hydrophobic crosslinked organopolysiloxane polymer and a liquid oil as ingredient H).

19. The cosmetic material according to claim 8, further comprising a silicone resin as ingredient I).

20. The cosmetic material according to claim 19, wherein the silicone resin of ingredient I) is an acrylic silicone resin.

21. The cosmetic material according to claim 19, wherein the silicone resin of ingredient I) is an acrylic silicone resin containing one or more organic groups selected from the group consisting of pyrrolidone, long-chain alkyl, polyoxyalkylene, fluoroalkyl and anionic carboxylic groups in the molecule.

22. The cosmetic material according to claim 19, wherein said ingredient I) is one or more types of silicone resin selected from among a group comprising silicone resins formed from $R^1_3SiO_{0.5}$ units and $SiO_2$ units, silicone resins formed from $R^1_3SiO_{0.5}$ units, $R^1_2SiO$ units and $SiO_2$ units, silicone resins formed from $R^1_3SiO_{0.5}$ units and $R^1SiO_{1.5}$ units, silicone resins formed from $R^1_3SiO_{0.5}$ units, $R^1_2SiO$ units and $R^1SiO_{1.5}$ units, and silicone resins formed from $R^1_3SiO_{0.5}$ units, $R^1_2SiO$ units, $R^1SiO_{1.5}$ units and $SiO_2$ units.

23. The cosmetic material according to claim 19, wherein said ingredient I) is a silicone resin containing one or more organic groups selected from among pyrrolidone, long-chain alkyl, polyoxyalkylene, fluoroalkyl and amino in the molecule.

24. A skin care cosmetic material containing the cosmetic material according to claim 8.

25. A makeup cosmetic material containing the cosmetic material according to claim 8.

26. A hair treatment cosmetic material containing the cosmetic material according to claim 8.

27. An antiperspirant cosmetic material containing the cosmetic material according to claim 8.

28. An ultraviolet protection cosmetic material containing the cosmetic material according to claim 8.

29. A cosmetic material containing the cosmetic material according to claim 8, said material being in the form of a liquid, emulsion, cream, solid, paste, gel, powder, press, laminate, mousse, spray or stick.

30. An organopolysiloxane polymer according to claim 2, wherein the liquid oil is selected from the group consisting of hydrocarbon oil, ester oil, natural animal and vegetable oils, and semi-synthetic oil.

31. An organopolysiloxane polymer according to claim 2, wherein the liquid oil is a silicone oil selected from the group consisting of dimethylpolysiloxane, methylphenylpolysiloxane, methylhydrogenpolysiloxane and dimethylsiloxane-methylphenyl siloxane copolymer, cyclosiloxanes, branched siloxanes, higher alkoxy-modified silicones, alkyl-modified silicones and amino-modified silicones.

* * * * *